(12) United States Patent
Spang et al.

(10) Patent No.: US 11,990,238 B2
(45) Date of Patent: May 21, 2024

(54) DECISION SUPPORT AND TREATMENT ADMINISTRATION SYSTEMS

(71) Applicant: DexCom, Inc., San Diego, CA (US)

(72) Inventors: Kathryn Yanli Spang, Cincinnati, OH (US); Sonya Ann Sokolash, Portland, OR (US); Douglas Scott Kanter, San Diego, CA (US); Janna Caryn Kimel, Portland, OR (US)

(73) Assignee: Dexcom, Inc., San Diego, CA (US)

( * ) Notice: Subject to any disclaimer, the term of this patent is extended or adjusted under 35 U.S.C. 154(b) by 155 days.

(21) Appl. No.: 17/154,182

(22) Filed: Jan. 21, 2021

(65) Prior Publication Data

US 2021/0257091 A1    Aug. 19, 2021

Related U.S. Application Data

(60) Provisional application No. 63/011,175, filed on Apr. 16, 2020, provisional application No. 62/976,778, filed on Feb. 14, 2020.

(51) Int. Cl.
*G16H 40/67* (2018.01)
*A61B 5/00* (2006.01)
(Continued)

(52) U.S. Cl.
CPC ......... *G16H 40/67* (2018.01); *A61B 5/14532* (2013.01); *A61B 5/4839* (2013.01);
(Continued)

(58) Field of Classification Search
CPC ........ G16H 20/17; G16H 40/67; G16H 20/60; G16H 10/40; G16H 50/20; A61B 5/14532;
(Continued)

(56) References Cited

U.S. PATENT DOCUMENTS 6,582,366 B1 *   6/2003   Porumbescu .......... G16H 50/50
                                                    600/300
2006/0276771 A1 * 12/2006  Galley ................. A61M 5/172
                                                    604/503
(Continued)

FOREIGN PATENT DOCUMENTS

CA          3089642 A1 *   8/2019   ........... A61B 5/0022
WO      WO-2011157372 A2 * 12/2011   ........... A61B 5/0002
(Continued)

OTHER PUBLICATIONS

Fletcher, Lauren, et al. "Feasibility of an implanted, closed-loop, blood-glucose control device." Immunology 230. (Year: 2001).*
(Continued)

*Primary Examiner* — Yi-Shan Yang
*Assistant Examiner* — Om Patel
(74) *Attorney, Agent, or Firm* — Patterson + Sheridan, LLP

(57) ABSTRACT

Techniques for data analysis and user guidance are provided for determining and providing one or more treatments to a user based on where the user is or will be in their menstrual cycle. In certain embodiments, a method of personalizing diabetes treatment based on information relating to a menstrual cycle of a user is provided. The method includes measuring, using a glucose monitoring system, blood glucose measurements of the user. The method further includes receiving information relating to the menstrual cycle of the user. The method further includes determining a treatment for the user to achieve a target blood glucose during a sub-phase or phase of the menstrual cycle of the user based on at least one of historical data associated with the user and historical data associated with a stratified group of users.

20 Claims, 6 Drawing Sheets

(51) Int. Cl.
  *A61B 5/145* (2006.01)
  *A61B 10/00* (2006.01)
  *G16H 10/40* (2018.01)
  *G16H 20/17* (2018.01)
  *G16H 20/60* (2018.01)

(52) U.S. Cl.
  CPC ............. *G16H 10/40* (2018.01); *G16H 20/17* (2018.01); *G16H 20/60* (2018.01); *A61B 10/0012* (2013.01)

(58) Field of Classification Search
  CPC . A61B 5/4839; A61B 10/0012; A61B 5/4306; A61B 5/4836; A61B 5/4842
  See application file for complete search history.

(56) References Cited

U.S. PATENT DOCUMENTS

| 2009/0118665 | A1 | 5/2009 | Estes et al. |
| 2013/0338630 | A1 | 12/2013 | Agrawal et al. |
| 2015/0217053 | A1 | 8/2015 | Booth et al. |
| 2016/0081597 | A1 | 3/2016 | Bhavaraju et al. |
| 2016/0113596 | A1 | 4/2016 | Koehler et al. |
| 2016/0328991 | A1* | 11/2016 | Simpson ............... A61B 5/1495 |
| 2017/0135643 | A1 | 5/2017 | Budiman et al. |
| 2017/0220750 | A1 | 8/2017 | Davis et al. |
| 2017/0220751 | A1* | 8/2017 | Davis .................... G06N 5/048 |
| 2017/0329917 | A1 | 11/2017 | McRaith et al. |
| 2019/0246973 | A1 | 8/2019 | Constantin et al. |

FOREIGN PATENT DOCUMENTS

| WO | WO-2014035672 A2 * | 3/2014 | ......... A61B 5/14532 |
| WO | WO-2019157102 A1 * | 8/2019 | ........... A61B 5/0022 |

OTHER PUBLICATIONS

Klonoff D.C., "Continuous Glucose Monitoring: Roadmap for 21$^{st}$ century diabetes therapy", Diabetes Care, May 2005, vol. 28, No. 5, pp. 1231-1239.

International Search Report and Written Opinion dated Apr. 28, 2021 for Application No. PCT/US2021/014305 in 11 pages.

* cited by examiner

DECISION SUPPORT AND TREATMENT ADMINISTRATION SYSTEMS

CROSS-REFERENCE TO RELATED APPLICATIONS

This application claims the benefits of U.S. Application Ser. No. 62/976,778 entitled "WOMEN'S HEALTH AND GLYCEMIC CONTROL," which was filed on Feb. 14, 2020 and U.S. Application Ser. No. 63/011,175 entitled "DECISION SUPPORT AND TREATMENT ADMINISTRATION SYSTEMS," which was filed on Apr. 16, 2020. The aforementioned provisional applications are herein incorporated by reference in their entirety.

BACKGROUND

Field

This application relates generally to medical devices such as analyte sensors, including systems and methods for using the same to provide treatments to a patient.

Description of the Related Technology

Diabetes is a metabolic condition relating to the production or use of insulin by the body. Insulin is a hormone that allows the body to use glucose for energy, or store glucose as fat.

When a person eats a meal that contains carbohydrates, the food is processed by the digestive system, which produces glucose in the person's blood. Blood glucose can be used for energy or stored as fat. The body normally maintains blood glucose levels in a range that provides sufficient energy to support bodily functions and avoids problems that can arise when glucose levels are too high, or too low. Regulation of blood glucose levels depends on the production and use of insulin, which regulates the movement of blood glucose into cells.

When the body does not produce enough insulin, or when the body is unable to effectively use insulin that is present, blood sugar levels can elevate beyond normal ranges. The state of having a higher than normal blood sugar level is called "hyperglycemia." Chronic hyperglycemia can lead to a number of health problems, such as cardiovascular disease, cataract and other eye problems, nerve damage (neuropathy), and kidney damage. Hyperglycemia can also lead to acute problems, such as diabetic ketoacidosis—a state in which the body becomes excessively acidic due to the presence of blood glucose and ketones, which are produced when the body cannot use glucose. The state of having lower than normal blood glucose levels is called "hypoglycemia." Severe hypoglycemia can lead to acute crises that can result in seizures or death.

A diabetes patient can receive insulin to manage blood glucose levels. Insulin can be received, for example, through a manual injection with a needle. Wearable insulin pumps are also available. Diet and exercise also affect blood glucose levels.

Diabetes conditions are sometimes referred to as "Type 1" and "Type 2." A Type 1 diabetes patient is typically able to use insulin when it is present, but the body is unable to produce sufficient amounts of insulin, because of a problem with the insulin-producing beta cells of the pancreas. A Type 2 diabetes patient may produce some insulin, but the patient has become "insulin resistant" due to a reduced sensitivity to insulin. The result is that even though insulin is present in the body, the insulin is not sufficiently used by the patient's body to effectively regulate blood sugar levels.

Management of diabetes can present complex challenges for patients, clinicians, and caregivers, as a confluence of many factors can impact a patient's glucose level and glucose trends. For example, a female patient's menstrual cycle can significantly impact the patient's insulin resistivity depending on which phase of the menstrual cycle the patient is in.

More specifically, a menstrual cycle typically lasts between 21 to 35 days, with an average of about 28 days. During this cycle, hormonal fluctuations not only trigger ovulation and menstruation but also impact the body's insulin resistivity. The menstrual cycle generally includes four phases including menstruation, the follicular phase, ovulation, and the luteal phase. During the luteal phase of the menstrual cycle, a hormone referred to as progesterone is released, which can cause insulin resistance and thereby leads to more hyperglycemic episodes, even if the patient follows the same exercise, diet, and/or insulin regimens. Accordingly, treatments suggested by a decision support system to a female patient, to help the patient with managing their glucose levels, may not be as effective during, for example, the luteal phase of the patient's menstrual cycle.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

One aspect is a system comprising: a glucose monitoring system, comprising: a glucose sensor configured to measure a blood glucose of a user, a sensor electronics module configured to transmit sensor data corresponding to blood glucose measurements provided by the glucose sensor to a processor; a memory circuit; the processor configured to: receive information relating to a menstrual cycle of the user, and determine a treatment for the user to achieve a target blood glucose during a sub-phase or phase of the menstrual cycle of the user based on at least one of historical data associated with the user and historical data associated with a stratified group of users, wherein: the historical data associated with the user includes blood glucose measurements of the user provided by the glucose monitoring system; the historical data associated with the user is structured such that it indicates at least one of: a pattern of at least one of the blood glucose measurements and insulin resistance of the user during the sub-phase or phase of the menstrual cycle of the user, and a pattern of physiological impact of the treatment on the blood glucose measurements of the user during the sub-phase or phase of the menstrual cycle of the user, the pattern indicating effectiveness of the treatment in regards to achieving the target blood glucose; and the historical data associated with the stratified group of users is structured such that it indicates at least one of: a pattern of at least one of blood glucose measurements and insulin resistance of the stratified group of users in the sub-phase or phase of the menstrual cycle, and a pattern of physiological impact of the treatment on the glucose measurements of the stratified group of users during the sub-phase or phase of the menstrual cycle, the pattern indicating effectiveness of the treatment in regards to achieving the target blood glucose.

In the above system, the processor is configured to provide the treatment. In the above system, the treatment comprises a dosage of insulin. In the above system, the dosage of insulin is higher than an average dosage of insulin administered to the user during non-luteal sub-phases or phases of the menstrual cycle of the user. In the above system, the processor is configured to transmit a signal to a medicament delivery device to administer the dosage of insulin to the user.

In the above system, the processor is configured to provide a therapy recommendation to the user or another individual, the therapy recommendation being indicative of the dosage of insulin. In the above system, the processor is configured to provide a therapy recommendation to the user or another individual, the therapy recommendation being indicative of at least one of an amount, type, length, and intensity of exercise. In the above system, the processor is configured to provide a therapy recommendation to the user or another individual, the therapy recommendation being indicative of at least one of an amount and type of food.

Another aspect is a method of personalizing diabetes treatment based on information relating to a menstrual cycle of a user, the method comprising: measuring, using a glucose monitoring system, blood glucose measurements of the user; receiving, at a processor in data communication with the glucose monitoring system, information relating to the menstrual cycle of the user; determining, at the processor, a treatment for the user to achieve a target blood glucose during a sub-phase or phase of the menstrual cycle of the user based on at least one of historical data associated with the user and historical data associated with a stratified group of users, wherein: the historical data associated with the user includes the blood glucose measurements of the user provided by the glucose monitoring system; the historical data associated with the user is structured such that it indicates at least one of: a pattern of at least one of the blood glucose measurements and insulin resistance of the user during the sub-phase or phase of the menstrual cycle of the user, and a pattern of physiological impact of the treatment on the blood glucose measurements of the user during the sub-phase or phase of the menstrual cycle of the user, the pattern indicating effectiveness of the treatment in regards to achieving the target blood glucose; and the historical data associated with the stratified group of users is structured such that it indicates at least one of: a pattern of at least one of blood glucose measurements and insulin resistance of the stratified group of users in the sub-phase or phase of the menstrual cycle, and a pattern of physiological impact of the treatment on the blood glucose measurements of the stratified group of users during the sub-phase or phase of the menstrual cycle, the pattern indicating effectiveness of the treatment in regards to achieving the target blood glucose.

The above method further comprises providing the treatment. In the above method, the treatment comprises a dosage of insulin. In the above method, the dosage of insulin is higher than an average dosage of insulin administered to the user during non-luteal sub-phases or phases of the menstrual cycle of the user. In the above method, providing the treatment further comprises transmitting a signal to a medicament delivery device to administer the dosage of insulin to the user. In the above method, providing the treatment further comprises providing a therapy recommendation to the user or another individual, the therapy recommendation being indicative of the dosage of insulin.

In the above method, providing the treatment further comprises providing a therapy recommendation to the user or another individual, the therapy recommendation being indicative of at least one of an amount, type, length, and intensity of exercise. In the above method, providing the treatment further comprises providing a therapy recommendation to the user or another individual, the therapy recommendation being indicative of at least one of an amount and type of food.

Another aspect is a non-transitory computer readable medium having instructions stored thereon that, when executed by a system, causes the system to perform a method comprising: measuring, using a glucose monitoring system, blood glucose measurements of the user; receiving, at a processor in data communication with the glucose monitoring system, information relating to the menstrual cycle of the user; determining, at the processor, a treatment for the user to achieve a target blood glucose during a sub-phase or phase of the menstrual cycle of the user based on at least one of historical data associated with the user and historical data associated with a stratified group of users, wherein: the historical data associated with the user includes the blood glucose measurements of the user provided by the glucose monitoring system; the historical data associated with the user is structured such that it indicates at least one of: a pattern of at least one of the blood glucose measurements and insulin resistance of the user during the sub-phase or phase of the menstrual cycle of the user, and a pattern of physiological impact of the treatment on the blood glucose measurements of the user during the sub-phase or phase of the menstrual cycle of the user, the pattern indicating effectiveness of the treatment in regards to achieving the target blood glucose; and the historical data associated with the stratified group of users is structured such that it indicates at least one of: a pattern of at least one of blood glucose measurements and insulin resistance of the stratified group of users in the sub-phase or phase of the menstrual cycle, and a pattern of physiological impact of the treatment on the blood glucose measurements of the stratified group of users during the sub-phase or phase of the menstrual cycle, the pattern indicating effectiveness of the treatment in regards to achieving the target blood glucose.

In the above medium, the method further comprises providing the treatment. In the above medium, the treatment comprises a dosage of insulin. In the above medium, the dosage of insulin is higher than an average dosage of insulin administered to the user during non-luteal sub-phases or phases of the menstrual cycle of the user.

Any of the features of an aspect is applicable to all aspects identified herein. Moreover, any of the features of an aspect is independently combinable, partly or wholly with other aspects described herein in any way, e.g., one, two, or three or more aspects may be combinable in whole or in part. Further, any of the features of an aspect may be made optional to other aspects. Any aspect of a method can comprise another aspect of a system for personalizing diabetes treatment based on information relating to a menstrual cycle of a user, and any aspect of a system for personalizing diabetes treatment based on information relating to a menstrual cycle of a user can be configured to perform a method of another aspect.

DETAILED DESCRIPTION

Figure 1A:
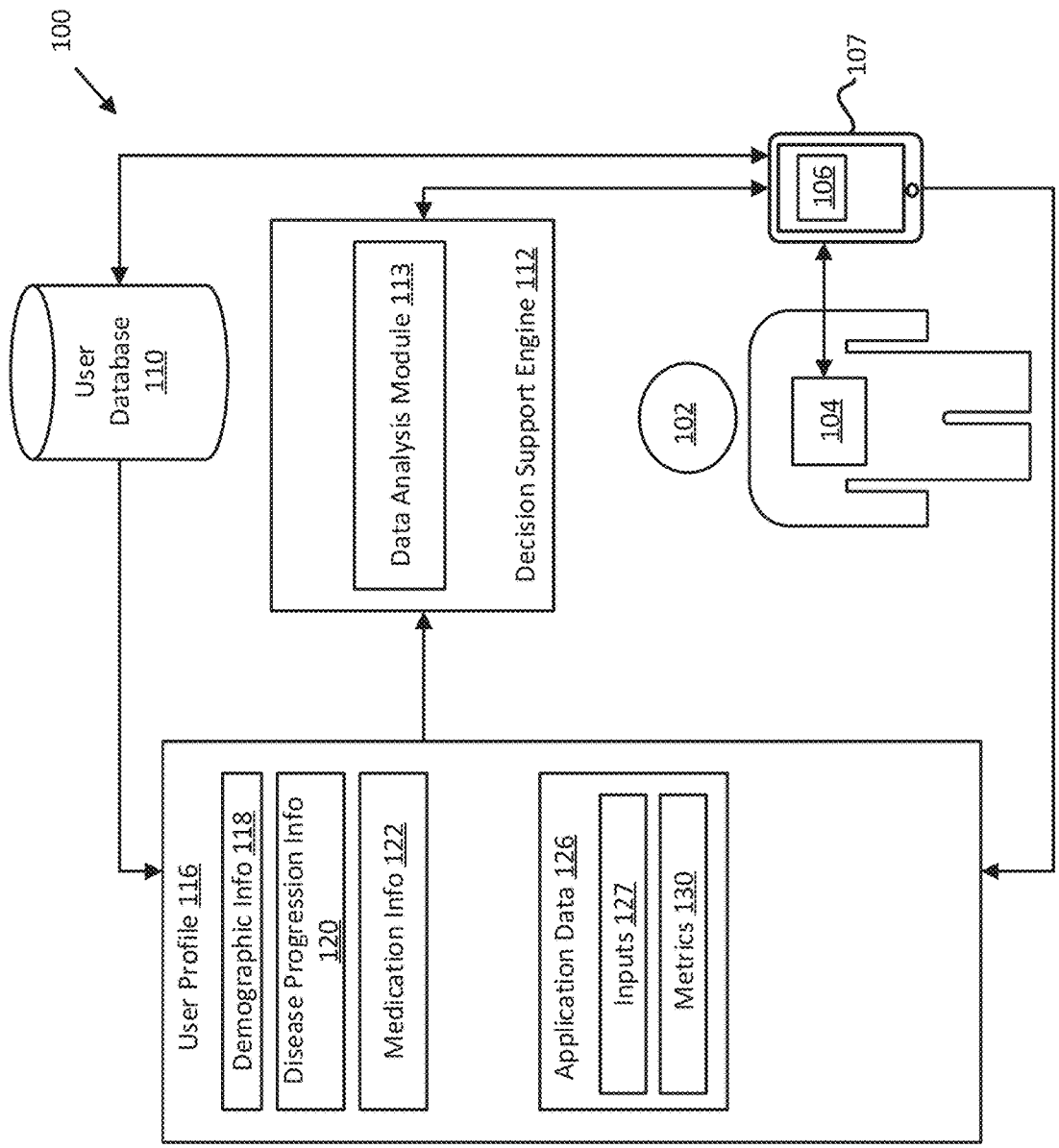
FIG. 1A illustrates an example decision support and treatment administration system ("DSTA"), according to some embodiments disclosed herein.

In certain embodiments, an application, as described herein, provides guidance and treatments that may assist patients, caregivers, healthcare providers, or other users improve lifestyle or clinical/patient outcomes by meeting a variety of challenges, such as overnight glucose control (e.g., reduce incidence of hypoglycemic events or hyperglycemic excursions), glucose control during and after meals (e.g. use historical information and trends to increase glycemic control), hyperglycemia corrections (e.g., increase time in target zone while avoiding hypoglycemic events from over-correction), hypoglycemia treatments (e.g., address hypoglycemia while avoiding "rebound" hyperglycemia), exercise, and/or other health factors. In certain embodiments, the application may further be configured with optimization tools that learn a patient's physiology and behavior and calculate guidance to help the patient identify optimal or desirable therapy parameters, such as basal insulin requirements, insulin to carb ratios, correction factors, and/or changes to insulin sensitivity due to exercise.

The application may, for example, help a patient respond to a problem in real time by predicting hypoglycemia or hyperglycemia events or trends, providing treatments to address occurring or potential hypoglycemia or hyperglycemia events or trends, and/or monitor the patient's glycemic, physiologic, and/or behavioral response to different events in real time. This type of calculated guidance and support may relieve the cognitive burden on the user.

Physiologic sensors such as continuous glucose monitors can provide useful data that may be used by a user to manage glucose levels, but the data may require significant processing to develop effective strategies for glucose management. The sheer volume of data, and recognition of correlations between types of data, trends, events, and outcomes, can far exceed human capabilities for processing. This is particularly impactful when a decision about therapy or response to a physiologic condition is being made in real time. Integration of real-time or recent data with historical data and patterns can provide useful guidance in making real-time decisions about therapy. Technological tools can process this information to provide decision support guidance calculated to be useful for a particular patient in a particular condition or situation at a particular time.

As described above, a female patient's menstrual cycle can significantly impact the patient's insulin resistivity depending on which phase of the menstrual cycle the patient is in. However, certain existing decision support systems do not take into account this change in insulin resistivity of the user. For example, it has been shown that in different phases, the patient has different levels of resistance to insulin. One example, though not limiting, is during the luteal phase. As such, during different phases of the menstrual cycle, an existing decision support system may continue to provide the same guidance (e.g., same insulin dosage, exercise, or dietary recommendations) without taking into account the phase of the menstrual cycle. As a result, a female user experiences frustration when the same treatment that was effective just a few days ago, is not as effective any more.

Further complicating this issue is the fact that insulin resistivity fluctuates by different amounts for different users. For example, during the luteal phase, a first female user experiences a 20% increase in insulin resistance while a second female user experiences a 40% increase in insulin resistance. This difference may be due to one or more factors including, but not limited to, age, weight, race, ethnicity, type of diet, other types of diseases that the user may have, etc. In addition, the type and amount of treatment that helps the first user combat her increase in insulin resistance may be different from the type and amount of treatment that helps a third user who also experiences a 20% increase in insulin resistance during different phases of the menstrual cycle. Further, the percentage by which the first user's insulin resistance varies during the menstrual cycle (e.g., increases during the luteal phase) may change over time due to numerous reasons including, but not limited to, age, change in weight, stress, pregnancy, other types of diseases, diet, etc.

Accordingly, certain embodiments described herein provide a technical solution to the technical problem described above in the field of diabetes intervention management. In certain embodiments, the technical solution provided herein improves existing decision support systems by configuring such systems to provide more accurate guidance and treatments based on where the user is in her menstrual cycle and further based on at least one of a record of the user's own historical data (e.g., how the user's physiology has reacted in the past during the same time/period in the user's menstrual cycle) and a record of historical data associated with one or more other users (e.g., how other similar users' (e.g., similarity based on the one or more factors) physiology reacted during the same time/period in the user's menstrual cycle). An integral part of the improved DSTA systems described herein is a glucose monitoring system 104, which includes a sensor electronics module and a continuous analyte sensor 140 (see FIG. 1B) that allow for continuously measuring the user's glucose levels and transmitting the glucose measurements, in real-time or near real-time, to one or more processors within the DSTA systems. Without receiving a continuous stream of glucose measurements from the glucose monitoring system 104 (e.g., in real-time or near real-time) it is difficult, if not possible, to provide treatments to a user that are relevant to the user's real-time glucose condition, considering the user's menstrual cycle. In other words, without the use of the glucose monitoring system 104, which improves the DSTA systems described herein, a user would be limited to certain existing techniques of measuring their glucose levels using finger sticks. However, it is extremely difficult, if not impossible or impractical, for a user to continuously (e.g., every five minutes) measure their glucose levels using finger picking techniques. Thus, without the use of the glucose monitoring system 104, described herein, the user's glucose measurements would be fragmented at best, thereby making the operations of the DSTA systems described herein difficult or causing them to provide potentially inaccurate or irrelevant treatments that are based on discontinuous and fragmented glucose measurements. As a result, the operations of the DSTA systems described herein are improved by or dependent on glucose monitoring system 104, which is able to provide a continuous and real or near real-time stream of glucose measurements.

In certain embodiments, the record of how the user's physiology reacted during the same time/period in the user's menstrual cycle may, among other things, include a record of how insulin resistant the user became during such time/period in previous cycles, the change in the user's glucose levels or other metrics in response to previously proposed treatments, etc. In certain embodiments, the record of how other similar users' physiology reacted during the same time/period may include, among other things, similar data about the physiology of such users. The accurate treatments may include various therapy recommendations to help the user manage their glucose level, for example, by keeping their glucose level in a desirable range, despite variations in insulin resistance during various phases of the menstrual cycle. The accurate treatments may include a certain insulin dosage calculated based on the factors above in order to help the user keep their glucose levels in range even in light of variations (e.g., increase) in insulin resistance. In certain embodiments, the insulin dosage may be provided to the user in the form of a therapy recommendation, based on which the user may administer (e.g., inject or orally consume) the insulin dosage manually. In certain embodiments, the insulin dosage may be signaled to a medicament delivery device (e.g., insulin pump or pen or another insulin administration device), based on which the medicament delivery device automatically administers the recommended dosage of insulin (e.g., after the user approves the recommended dosage).

The accurate treatments may additionally or instead include a therapy recommendation for the user to engage in a certain amount and/or type of exercise to lower her glucose levels back into range. In addition, the accurate treatments may additionally or instead include a therapy recommendation for consuming and/or abstaining from consuming certain amounts or types of foods and/or for a certain period of time to lower her glucose levels back into range. Providing accurate therapy recommendations (e.g., insulin or other medicament dosage, activity, carbohydrate intake, etc.) no matter where the user is in their menstrual cycle is an improvement to the existing decision support systems that leads to significant health improvement and user outcome.

As described above, in certain embodiments, to provide relevant and effective guidance and treatments, the application utilizes input from one or more physiological sensors, such as one or more analyte sensors. An example of an analyte sensor described herein is a glucose monitoring sensor that measures a concentration of glucose and/or a substance indicative of the concentration or presence of glucose and/or another analyte in the user's body. In some embodiments, the glucose monitoring sensor is a continuous glucose monitoring device such as a subcutaneous, transdermal, transcutaneous, non-invasive, intraocular and/or intravascular (e.g., intravenous) device. In some embodiments, the device can analyze a plurality of intermittent blood samples. The glucose monitoring sensor can use any method of glucose measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose monitoring sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (HCP, e.g., doctor, physician, nurse, caregiver), who may be using the sensor.

In some embodiments, the glucose monitoring sensor is an implantable sensor, such as described with reference to U.S. Pat. No. 6,001,067 and U.S. Patent Publication No. US-2011-0027127-A1. In some embodiments, the glucose monitoring sensor is a transcutaneous sensor, such as described with reference to U.S. Patent Publication No. US-2006-0020187-A1. In yet other embodiments, the glucose monitoring sensor is a dual electrode analyte sensor, such as described with reference to U.S. Patent Publication No. US-2009-0137887-A1. In still other embodiments, the glucose monitoring sensor is configured to be implanted in a host vessel or extracorporeally, such as the sensor described in U.S. Patent Publication No. US-2007-0027385-A1. These patents and publications are incorporated herein by reference in their entirety.

Example System

FIG. 1A illustrates an example DSTA 100 including a diabetes intervention application ("application") 106 that provides decision-support guidance to and determines/administers one or more treatments for user 102 (hereinafter "the user"), in certain embodiments. The user, in certain embodiments, may be the patient or the patient's caregiver. In the embodiments described herein, the user is assumed to be the patient for simplicity only but is not so limited. In certain embodiments, DSTA 100 includes the user, a glucose monitoring system 104, a mobile device 107 that executes application 106, a decision support engine 112, an optional insulin administration device (not shown), and a user database 110.

In certain embodiments, glucose monitoring system 104 includes a sensor electronics module and a glucose sensor that measures a concentration of blood glucose and/or a substance indicative of the concentration or presence of glucose and/or another analyte in the user's body. In certain embodiments, the glucose sensor is configured to perform measurements on a continuous basis. The sensor electronics module transmits the blood glucose measurements to mobile device 107 for use by application 106. In some embodiments, the sensor electronics module transmits the glucose measurements to mobile device 107 through a wireless connection (e.g., Bluetooth connection). In certain embodiments, mobile device 107 is a smart phone. However, in certain embodiments, mobile device 107 may instead be any other type of computing device such as a laptop computer, a smart watch, a tablet, or any other computing device capable of executing application 106.

In certain embodiments, decision support engine 112 refers to a set of software instructions with one or more software modules, including a data analysis module (DAM) 113. In some embodiments, decision support engine 112 executes entirely on one or more computing devices in a private or a public cloud. In such embodiments, application 106 communicates with decision support engine 112 over a network (e.g., Internet). In some other embodiments, decision support engine 112 executes partially on one or more local devices, such as mobile device 107, and partially on one or more computing devices in a private or a public cloud. In some other embodiments, decision support engine 112 executes entirely on one or more local devices, such as mobile device 107.

In certain embodiments, DAM 113 is configured to process a set of inputs received from application 106 and compute a plurality of metrics 130, which can then be stored in user profile 116. Inputs 127 and metrics 130 may be used by application 106, such as by different features of application 106, to provide real-time guidance and treatments to the user. The various data points of user profile 116 are described in further detail below. In certain embodiments, user profiles, including user profile 116, are stored in a user database 110, which is accessible to application 106 as well as decision support engine 112 over one or more networks (not shown). User database 110, in some embodiments, refers to a storage server that may operate in a public or private cloud.

The real-time guidance and treatments provided to the user help improve the user's physiological conditions and/or enable the user with making more informed decisions. To provide effective, relevant, and on-time guidance and treatments to the user, in certain embodiments, a feature of application 106 may take as input information relating to the user, which is stored in user profile 116, and/or information relating to a pool of similar users, which is stored in user profiles of such users in user database 110. In certain embodiments, a feature of application 106 may interact with the user through various ways such as text, email, notifications (e.g., push notifications), phone calls, and/or other forms of communication such as displaying content (e.g., graphs, trends, charts, etc.) on the user interface of application 106.

As described above, in certain embodiments, application 106 is configured to take as input information relating to the user and store the information in a user profile 116 of the user. For example, application 106 may obtain and record the user's demographic info 118, disease progression info 120, and/or medication info 122 in user profile 116. In certain embodiments, demographic info 118 may include one or more of the user's age, BMI (body mass index), ethnicity, gender, etc. In certain embodiments, disease progression info 120 may include information about the user's disease, such as whether the user is Type I, Type II, or pre-diabetic or whether the user has gestational diabetes. In certain embodiments, information about the user's disease may also include the length of time since diagnosis, the level of diabetes control, level of compliance with diabetes management therapy, predicted pancreatic function, other types of diagnosis (e.g., heart disease, obesity) or measures of health (e.g., heart rate, exercise, stress, sleep, etc.), and/or the like. In certain embodiments, medication regimen info 122 may include information about the amount and type of insulin or non-insulin diabetes medications and/or non-diabetes medication taken by the user. In certain embodiments, application 106 may obtain demographic info 118, disease progression info 120, and/or medication info 122 from the user in the form of user input or from other sources. In certain embodiments, as some of this information changes, application 106 may receive updates from the user or other sources.

In certain embodiments, in addition to the user's demographic info 118, disease progression info 120, and/or medication info 122, application 106 obtains an additional set of inputs 127 that are also utilized by the various features of application 106 to provide guidance to the user. In certain embodiments, such inputs 127 are obtained on a continuous basis. In certain embodiments, application 106 receives inputs 127 through user input and/or a plurality of other sources, including glucose monitoring system 104, other applications running on mobile device 107, such as a menstrual cycle management application, and/or one or more other sensors and devices. In certain embodiments, such sensors and devices include one or more of, but are not limited to, an insulin administration device, other types of analyte sensors, sensors or devices provided by mobile device 107 (e.g., accelerometer, camera, global positioning system (GPS), heart rate monitor, etc.) or other user accessories (e.g., a smart watch), or any other sensors or devices that provide relevant information about the user.

In certain embodiments, application 106 further uses at least a portion of inputs 127 to obtain a plurality of metrics, such as metrics 130, which are also stored in user profile 116. As further described in relation to FIG. 2, in some embodiments, application 106 transmits at least a portion of inputs 127 to DAM 113 for processing, based on which DAM 113 generates metrics 130. In certain embodiments, metrics 130 may then be used by application 106 as input for providing guidance to the user. Note that, in certain embodiments, user profile 116 and the user profiles of a pool of users in user database 110 are dynamic, because information in the user profiles, including user profile 116, may change as new inputs 127 are regularly received or as existing information in the user profiles is changed (e.g., the user's medication info changes, etc.)

Figure 2:
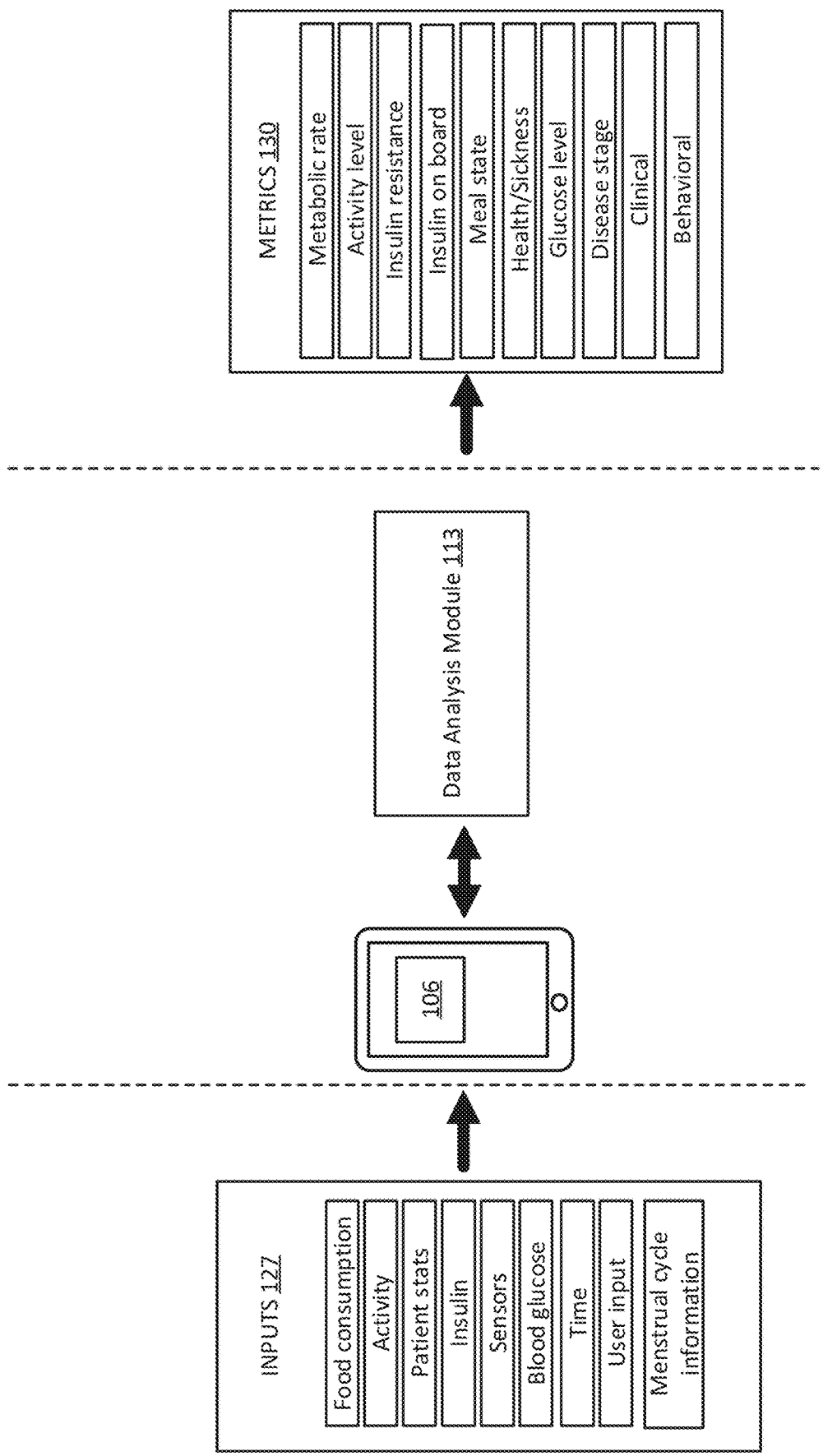
FIG. 2 illustrates example inputs and example metrics that are calculated based on the inputs for use by the DSTA of FIG. 1A, according to some embodiments disclosed herein.

As further described in relation to FIG. 2, in certain embodiments, metrics 130 may, at least in some cases, be generally indicative of the user's current or future health or state, such as one or more of the user's physiological (e.g., glucose level, insulin resistance, etc.) or psychological state (e.g., stress level, happiness, etc.), trends associated with the user's health or state, etc. For examples, metrics 130 may include one or more of metrics associated with metabolic rates, glucose levels and trends, the user's health or sickness, etc. Metrics 130 may also include behavioral metrics that may be indicative of the user's behaviors and habits, such meal habits, exercise regimen, etc. In certain embodiments, metrics 130 may include real-time metrics, past metrics, and/or trends.

Although not limited to this list, some example features of application 106 may include one or more of a reporting feature, intervention features, a medication reminder feature, a glycemic impact estimator feature, an educational feature, etc.

In certain embodiments, a reporting feature may provide reports to the user in various forms. For example, a reporting feature may be configured to isolate and report glycemic excursions to the user so as to enable the user to think through the causes of such glycemic excursions. In certain embodiments, a reporting feature may provide a report that combines glucose, insulin, and menstrual cycle information of the user. For example, a report may indicate how the user's glucose levels and insulin resistance changed in relation to the different phases of the user's menstrual cycle. In certain embodiments, a report (e.g., real-time) may remind the user about where the user is in their menstrual cycle and indicate that a glycemic excursion the user is currently experiencing is due to that factor. In certain embodiments, a report may remind the user about where the user is in their menstrual cycle and further warn or inform the user that she will be experiencing a glycemic excursion in 2 days because, for example, the user is entering the luteal phase in 2 days.

Further, a report may be provided to the user in various forms, as one of ordinary skill in the art appreciates. For example, a reporting feature may display a graph of the user's glucose measurement trends with two glycemic excursions highlighted with text that says, "you had two high glucose events today; the first lasted for 55 minutes and the second lasted 30 minutes." In one example, a graph of the user's glucose measurement trends or predictions may be supplemented with a timeline of the user's menstrual cycle to show, for instance, why the user is experiencing higher than usual glucose levels, why the user will experience higher than usual glucose levels on certain future dates (e.g., if the user does not consume or engage in any treatment), etc. Combining the user's past, current, and/or predicted physiological stats with information about the user's menstrual cycle enables the user to make informed decisions about the available treatment options that may be provided by DSTA 100.

In one example the reporting feature may provide an afternoon report that provides information about the user's blood glucose average so far for that day, indicate a rest-of-day average required to keep on track towards the user's target glucose range, and recommend a low glycemic load or physical activity. In another example, the reporting feature may provide a nighttime summary that includes daily, weekly, and monthly blood glucose averages, and estimated A1c. For example, the summary informs the user of what the next day's blood glucose average must be in order for the user to attain their A1c goal.

In certain embodiments, a reporting feature may be focused on providing the user with teachable moments. In certain embodiments, a teachable moment identifies the effect of behavior (e.g., physical activity, diet, medication adherence, and/or sleep) on blood sugar. Teachable moments may be pushed to the user in the form of notification and/or recorded on a glucose monitoring curve to be reviewed in a timely manner by the user. For example, teachable moments may be visually displayed on the curve and describe the behavior and glucose response in order to inform the user as to what behavior caused what glucose response.

An example of a positive teaching moment may be provided when the user eats a high glycemic load breakfast that raises their blood sugar around 10AM. In certain embodiments, based on input from the user's accelerometer, the reporting feature may then determine that the user went for a 30-minute walk, which caused the user's blood glucose to return to their target range. In certain embodiments, the reporting feature marks this event as a teachable moment (e.g., by displaying a star on CGM curve) and may send a notification to the user, stating: "Nice walking, Sharon! Because of your 30-minute walk, your blood sugar is now right back where you want it."

In certain embodiments, intervention features include any feature that operates to change the user's actions, such as by encouraging the user to engage in a certain action or to refrain from engaging in a certain action. As an example, an intervention feature may be configured to send push notifications to the user to encourage the user to engage in a certain action. The intervention feature may also be able to determine that a user is about to engage in a certain action, for example, based on the user's past actions, and send a push notification to the user to not engage in such action. In some embodiments, push notifications to the user may be based on information relating to the user (e.g., inputs 127, metrics 130, etc.) and/or information relating to a stratified group of users.

For example, a type of an intervention feature may involve exercise management. An example includes an exercise management feature that encourages the user, e.g., through a push notification, to exercise upon determining that the user's glucose levels are or will be high or at a level where lack of exercise may cause the user's glucose levels to increase. As an example, based on where the user is in their menstrual cycle as well as information relating to the user and/or information relating to a group of similar users, the exercise management feature may recommend that the user exercise for an additional 2 hours during the next few days because the user is starting to enter the luteal phase.

In certain embodiments, the exercise management feature may be configured to receive and analyze data from an accelerometer, a global positioning system (GPS), a heartbeat monitoring sensor, glucose monitoring system 104, and/or other types of sensors and devices in order to provide more effective and tailored guidance to the user. For example, by receiving information from one or more of these sensors and devices, an exercise management feature may be able to make a determination as to whether the user actually engaged in an exercise, for how long the user should exercise to ensure the user's blood glucose gets back into normal range, what walking route should the user take, etc.

Another type of an intervention feature may involve diet management. For example, a diet management feature may act as a virtual dietician for providing guidance to the user as to one or more of when to eat, what to eat, how much to eat, etc. In certain embodiments, the diet management feature may provide personalized meal recommendations based on one or more of the user's real-time conditions (e.g., real-time blood glucose measurements), the user's body's response to certain meals, etc. In certain embodiments, the diet management feature may also help the user with meal prepping and/or shopping and/or allow the user to enter information about meals consumed by the user to understand nutritional values, etc. In certain embodiments, the diet management feature may further make menu and ingredient substitution suggestions at restaurants or suggest healthy restaurants and grocery stores within a certain geographical area. In certain embodiments, based on where the user is in their menstrual cycle as well as information relating to the user and/or information relating to a group of similar users, the diet management feature may recommend that the user changes their diet, for example, during the next few days because the user is starting to enter the luteal phase. For example, the diet management feature may calculate portions or amounts of different types of food (e.g. carbs, sweets, etc.) that the user can consume and still be within a target glucose range. The diet management feature may also remind the user to refrain from consuming certain types of food or more than a certain amount of such foods because the user is or will be insulin resistant for a certain period.

In certain embodiments, the diet management feature may also provide notifications based on information about the user's meal information. For example, if the user has had a meal and their blood glucose does not lower back into a target zone afterwards (e.g., the next pre-prandial peak (2 hours after initial meal-related glucose rise) is more than 180 mg/dL), then an urgent alert may be issued to the user to exercise immediately. However, if the user's last meal had a prost-prandial peak of less than 180 mg/dL, and pre-prandial glucose is in range (80-130), then the diet management feature may randomize if the user receives an alert after the next meal (e.g., reduce the likelihood of sending an alert by 33%). Note that the exercise and diet management features described above are merely two examples of intervention features.

In certain embodiments, the medication management feature may provide notifications to the user for when the user needs to take medication, what type of medication (e.g., oral medication for Type II diabetic patients, and insulin injection for Type I diabetic patients, etc.) the user should take, in what dosage or amount, etc. A medication management feature may provide such notifications based on the user's specific information, such as the user's disease (e.g., Type I or Type II), current and predicted metrics 130 (e.g., current blood levels and metrics), the user's menstrual cycle information, information relating to a similar group of users, etc. For example, the medication management feature may be configured to learn over a certain amount of time (e.g., a few months) how insulin resistant the user becomes during certain dates of the menstrual cycle and how much more basal insulin needs to be administered to the user during those dates or in preparation for those dates. As a more specific example, the medication management feature may determine that it is now two days prior to the user entering the luteal phase and ask the user to either administer twice the amount of basal insulin in preparation for the user becoming insulin resistant or ask the user whether it is okay to signal the user's insulin pump to automatically start administering twice the amount of basal insulin. In another example, the medication management feature may detect that the user is beginning to become insulin resistant and recommend administering twice the amount of basal insulin as the user typically administers on days where the user is not insulin resistant.

In certain embodiments, the medication management feature may determine that, based on the user's historical information, a certain additional dosage of basal insulin administered during a certain phase of the user's menstrual cycle (e.g., luteal phase) had been successful in maintaining the user's glucose levels in range. In such an example, the medication management feature may recommend that the user administer that additional dosage or automatically direct an insulin pump to administer the additional dosage during or in anticipation of the user's increase in insulin resistivity because of hormonal changes during the menstrual cycle. In certain embodiments, the medication management feature may determine how much additional insulin should be administered to the user based on what has been effective for a group of similar users.

In certain embodiments, the learning process involved in determining an appropriate amount of additional insulin to administer, to combat the change (e.g., increase) in insulin resistance due to the user's menstrual cycle, involves examining user's historical information, such as patterns relating to how insulin resistant the user becomes during certain dates, how much insulin it generally takes to bring the user's glucose levels back into range, the user's time-in-range during certain dates in light of the amount of insulin they took, and/or similar information associated with one or more similar users, etc. For example, in certain embodiments, the medication management feature may learn that in month X, during certain cycle-related dates, it recommended that the user take 1.5 times the amount of basal insulin the user normally takes but the user's glucose levels did not come back in range or the user spent more time out of range than desired. Based on that, in certain embodiments, the application may recalculate the dosage and, during the same dates in month X+1, recommend that the user take 1.7 times the amount of basal insulin the user typically takes. Based on the pattern of insulin dosage recommendation and the user's physiological reaction (e.g., time-in-range), the medication management feature may eventually learn (e.g., through DAM 113, as described below) an appropriate amount of insulin to recommend to the user depending on where the user is in their menstrual cycle.

In certain embodiments, the medication management feature may also keep track of how well the user has been following the medication schedule, order medication for the user automatically before the user runs out of the medication, and/or provide information about the medication itself (e.g., educate the user on the medication's impact and efficacy). For example, the medication management feature may query the patient as to whether they took their medication. If user answers "yes" three times in a row, then the medication management feature may randomize and assign a 33% chance for asking the user the next day. If the user does not answer "yes" three times in a row, then the medication management feature may send a reminder to the user to take their medication the next day.

In certain embodiments, as described above, the medication management feature may automatically communicate with an insulin administration device, such as a pump or pen, to cause the device to administer the right dosage of insulin, based on the user's current or predicted metrics 130. For example, the medication management feature may take into account the user's current glucose levels and metrics as well as the user's predicted glucose levels and metrics and determine an accurate amount of long-lasting insulin to be administered. In certain embodiments, the medication management feature may then send signals to the medicament administration device to administer the said amount of insulin. As described above, in certain embodiments, the medication management feature takes information relating to the user and/or information relating to the stratified group of users into account calculating the amount of insulin to be administered. Example details relating to how DSTA 100 (including application 106) is able to set insulin rates of an insulin administration device (also referred to as a medicament delivery device) are described in paragraphs [0425]-[0426] of U.S. Pat. App. Pub. 2019/0246973, which is incorporated herein in its entirety.

In certain embodiments, the glycemic impact estimator feature may use mobile device 107's camera to scan a menu and convert each meal item into an estimated glycemic impact metric. In some embodiments, the glycemic impact estimator feature shows glycemic impact metrics superimposed over the menu items. In some embodiments, glycemic impact metrics are based on data from user profiles of a stratified group of users. In some embodiments, the glycemic impact estimator feature may highlight different menu items based on how healthy the items are using different coloring (e.g., green for healthier items and red for unhealthy items).

In certain embodiments, the educational feature educates the user about the user's condition and how the user can improve his/her health. In one example, the educational feature educates the user about the potential impact the user may see if the user adopts a certain lifestyle. In certain embodiments, to determine the potential impact, the educational feature may consider the impact other users in the stratified group, who adopted that same lifestyle, experienced. For example, the educational feature may state to the user: "by following this program, patients like you were able to lower their A1C by 5% during their luteal phase." In certain embodiments, the educational feature may also educate the user about the cause and effect of potential behaviors, such as based on the effects users in the stratified group experienced.

In certain embodiments, the educational feature provides alternatives to administering insulin or higher than desired amounts of insulin during certain periods in the user's menstrual cycle. For example, the educational feature may examine information relating to the stratified group of users and find that certain users in the group were able to maintain their glucose in the target range by exercising for an additional hour during the luteal phase without taking any higher-than-usual amounts of insulin. In such an example, the educational feature may then inform the user about this finding. Note that based on this finding, the exercise management feature may also recommend that the user engage in an extra one-hour exercise during the luteal phase and additionally recommend the type and intensity of the exercise based on the user's habits. In another example, the educational feature may examine information relating to the stratified group of users and find that certain users in the group were able to maintain their glucose in the target range by consuming less of certain foods during the luteal phase without taking any higher-than-usual amounts of insulin. Similarly, in such an example, the educational feature may inform the user about this finding and the diet management feature may recommend specifically how the user can change their diet, what portions to eat, etc., based on the same finding.

Figure 1B:
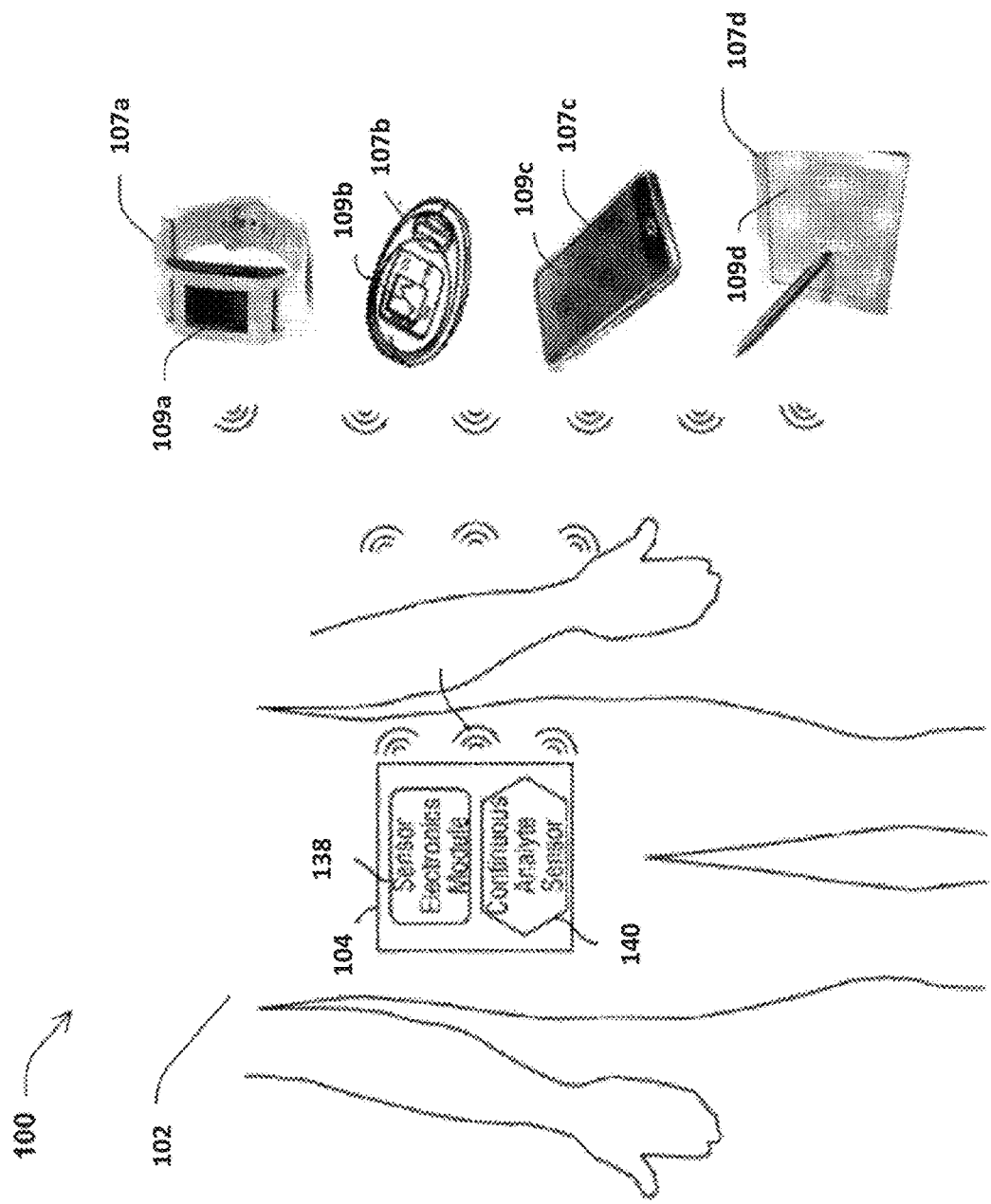
FIG. 1B illustrates the example glucose monitoring system of FIG. 1A, in more detail, along with a number of mobile devices, according to some embodiments disclosed herein.

FIG. 1B illustrates glucose monitoring system 104 in more detail. FIG. 1B also illustrates a number of mobile devices 107a, 107b, 107c, and 107d. Note that mobile device 107 of FIG. 1A may be any one of mobile devices 107a, 107b, 107c, or 107d. In other words, any one of mobile devices 107a, 107b, 107c, or 107d may be configured to execute application 106. Glucose monitoring system 104 may be communicatively coupled to mobile devices 107a, 107b, 107c, and/or 107d. Glucose monitoring system 104 may be communicatively coupled to an insulin administration device (not shown) that may also be placed on the user's body for administering insulin to the user's body.

By way of an overview and an example, glucose monitoring system 104 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices, such as mobile devices 107a, 107b, 107c, and/or 107d. Paragraphs [0137]-[0140] and FIGS. 3A, 3B, and 4 of U.S. App. No. 2019/0336053 further describe an on-skin sensor assembly that, in certain embodiments, may be used in connection with glucose monitoring system 104. Paragraphs [0137]-[0140] and FIGS. 3A, 3B, and 4 of U.S. App. No. 2019/0336053 are incorporated herein by reference.

In certain embodiments, glucose monitoring system 104 includes an analyte sensor electronics module 138 and a glucose sensor 140 associated with analyte sensor electronics module 138. In certain embodiments, analyte sensor electronics module 138 includes electronic circuitry associated with measuring and processing analyte sensor data or information, including algorithms associated with processing and/or calibration of the analyte sensor data/information. Analyte sensor electronics module 138 may be physically/mechanically connected to glucose sensor 140 and can be integral with (i.e., non-releasably attached to) or releasably attachable to glucose sensor 140.

Analyte sensor electronics module 138 may also be electrically coupled to glucose sensor 140, such that the components may be electromechanically coupled to one another. Analyte sensor electronics module 138 may include hardware, firmware, and/or software that enable measurement and/or estimation of levels of the analyte in the user via glucose sensor 140 (e.g., which may be/include a glucose sensor). For example, analyte sensor electronics module 138 can include one or more potentiostats, a power source for providing power to glucose sensor 140, other components useful for signal processing and data storage, and a telemetry module for transmitting data from the sensor electronics module to one or more display devices. Electronics can be affixed to a printed circuit board (PCB) within glucose monitoring system 104, or platform or the like, and can take a variety of forms. For example, the electronics can take the form of an integrated circuit (IC), such as an application-specific integrated circuit (ASIC), a microcontroller, a processor, and/or a state machine.

Analyte sensor electronics module 138 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

Glucose sensor 140 is configured to measure a concentration or level of the analyte in the user 102. The term analyte is further defined by paragraph of U.S. App. No. 2019/0336053. Paragraph of U.S. App. No. 2019/0336053 is incorporated herein by reference. In some embodiments, glucose sensor 140 comprises a continuous glucose sensor, such as a subcutaneous, transdermal (e.g., transcutaneous), or intravascular device. In some embodiments, glucose sensor 140 can analyze a plurality of intermittent blood samples. Glucose sensor 140 can use any method of glucose-measurement, including enzymatic, chemical, physical, electrochemical, spectrophotometric, polarimetric, calorimetric, iontophoretic, radiometric, immunochemical, and the like. Additional details relating to a continuous glucose sensor are provided in paragraphs [0072]-[0076] of U.S. application Ser. No. 13/827,577. Paragraphs [0072]-[0076] of U.S. application Ser. No. 13/827,577 are incorporated herein by reference.

With further reference to FIG. 1B, mobile devices 107a, 107b, 107c, and/or 107d can be configured for displaying (and/or alarming) displayable sensor information that may be transmitted by sensor electronics module 138 (e.g., in a customized data package that is transmitted to the display devices based on their respective preferences). Each of mobile devices 107a, 107b, 107c, and/or 107d may respectively include a display such as touchscreen display 109a, 109b, 109c, and/or 109d for displaying a graphical user interface of application 106 for presenting sensor information and/or analyte data to user 102 and/or receiving inputs from user 102. In certain embodiments, the mobile devices may include other types of user interfaces such as voice user interface instead of or in addition to a touchscreen display for communicating sensor information to user 102 of the mobile device and/or receiving user inputs. In certain embodiments, one, some, or all of mobile devices 107a, 107b, 107c, and/or 107d may be configured to display or otherwise communicate the sensor information as it is communicated from sensor electronics module 138 (e.g., in a data package that is transmitted to respective display devices), without any additional prospective processing required for calibration and/or real-time display of the sensor data.

The plurality of mobile devices 107a, 107b, 107c, and/or 107d depicted in FIG. 1B may include a custom or proprietary display device, for example, analyte display device 107b, especially designed for displaying certain types of displayable sensor information associated with analyte data received from sensor electronics module 138 (e.g., a numerical value and/or an arrow, in certain embodiments). In certain embodiments, one of the plurality of mobile devices 107a, 107b, 107c, and/or 107d includes a smartphone, such as mobile phone 107c, based on an Android, iOS, or another operating system configured to display a graphical representation of the continuous sensor data (e.g., including current and/or historical data).

FIG. 2 provides a more detailed illustration of example inputs and example metrics that are determined based on the inputs, in accordance with certain embodiments. FIG. 2 illustrates example inputs 127 on the left, application 106 and DAM 113 in the middle, and metrics 130 on the right. In certain embodiments, each metric may correspond to one or more values, e.g., discrete numerical values, ranges, or qualitative values (high/medium/low or stable/unstable.). Application 106 obtains inputs 127 through one or more channels (e.g., manual user input, sensors, other applications executing on mobile device 107, etc.). In certain embodiments, inputs 127 may be used by the features of application 106 to provide guidance and treatment to the user (e.g., including signaling an insulin pump to administer a certain dosage of insulin). Inputs 127 may also be further processed by DAM 113 to output a plurality of metrics, such as metrics 130, which may similarly be used by the features of application 106 to provide guidance and treatment to the user.

As shown, inputs 127 include, but are not limited to, food consumption information, activity information, patient stats, insulin information, information from the sensors, blood glucose information, time, calendar, user input, menstrual cycle information, etc.

Food consumption information may include information about one or more of meals, snacks, and/or beverages, such as one or more of the size, content (carbohydrate, fat, protein, etc.), sequence of consumption, and time of consumption. In certain embodiments, food consumption may be provided by a user through manual entry, by providing a photograph through an application that is configured to recognize food types and quantities, and/or by scanning a bar code or menu. In various examples, meal size may be manually entered as one or more of calories, quantity ('three cookies'), menu items ('Royale with Cheese'), and/or food exchanges (1 fruit, 1 dairy). In some examples, meals may also be entered with the user's typical items or combinations for this time or context (e.g., workday breakfast at home, weekend brunch at restaurant). In some examples, meal information may be received via a convenient user interface provided by application 106.

In certain embodiments, activity information is also provided as an input. Activity information may be provided, for example, by an accelerometer sensor on a wearable device such as a watch, fitness tracker, and/or patch. In certain embodiments, activity information may also be provided through manual user input.

In certain embodiments, patient statistics, such as one or more of age, height, weight, body mass index, body composition (e.g., % body fat), stature, build, or other information may also be provided. In certain embodiments, patient statistics are provided through a user interface, by interfacing with an electronic source such as an electronic medical record, and/or from measurement devices. In certain embodiments, the measurement devices include one or more of a wireless, e.g., Bluetooth-enabled, weight scale and/or camera, which may, for example, communicate with the mobile device 107 to provide patient data.

In certain embodiments, input relating to the patient's insulin delivery may be received, via a wireless connection on a smart pen, via user input, and/or from an insulin pump (a type of insulin administration device). Insulin delivery information may include one or more of insulin volume, time of delivery, etc. Other parameters, such as insulin action time or duration of insulin action, may also be received as inputs.

In certain embodiments, input may also be received from sensors, such as physiologic sensors, which may detect one or more of heart rate, respiration, oxygen saturation, or body temperature (e.g. to detect illness). In certain embodiments, electromagnetic sensors may also detect low-power RF fields emitted from objects or tools touching or near the object, which may provide information about the patient activity or location. An example of information that can be received from sensors is the user's blood glucose values.

In certain embodiments, blood glucose information may also be provided as input, for example through a glucose monitoring system 104. Blood glucose information may include any glucose-related measurements known in the art. In certain embodiments, blood glucose information may be received from one or more of smart pill dispensers that track when the user takes medicine, a blood ketone meter, a laboratory-measured or estimated A1C, other measures of long-term control, or sensors that measure peripheral neuropathy using tactile response, such as by using haptic features of a smartphone, or a specialty device.

In certain embodiments, time may also be provided as an input, such as time of day, or time from a real-time clock. Time also includes date, month, and year.

User input through a user interface, such a user interface of mobile device 107, may include any other types of inputs a user may provide to application 106, such as the other types of inputs mentioned above. For example, in certain embodiments, user input may include one or more of the type of amount of food consumed, the delivery of therapy, such as the use of glucagon to stimulate liver release of glycogen in response to a low blood sugar, recommended basal rates or insulin-to-carb ratios (e.g. received from a clinician), recorded activity (e.g. intensity, duration and time completed or started), etc. In certain embodiments, the user input may also indicate medication intake (e.g., type and dosage of medication as well as the timing of when medication is taken).

In certain embodiments, inputs 127 further include information about the user's menstrual cycle. As described above, this information may be received from a third-party application, such as a period tracking application. The third party application, in certain embodiments, may regularly interface with the application 106 through, for example, an application programming interface. Information about the user's menstrual cycle may include information about one or more of the different phases of the user's cycle, how long each takes, the corresponding dates, predicted dates for when the user will be entering each phase, what phase the user is in currently, when the current date is expected to end, and so on. In certain embodiments, the user my supplement the information provided by the third party application with user input. For example, the user may provide input that the user's menstruation phase just started, etc. In certain embodiments, application 106 may not rely on any input from a third party application and instead only rely on user input. In such embodiments, for example, application 106 may calculate information about the user's menstrual cycle based on the user input and/or certain scientific-based logic.

As described above, in certain embodiments, DAM 113 determines or computes the user's metrics 130 based on inputs 127. An example list of metrics 130 is shown in FIG. 2.

In certain embodiments, a metabolic rate is a metric that may indicate or include a basal metabolic rate (e.g., energy consumed at rest) and/or an active metabolism, e.g., energy consumed by activity, such as exercise or exertion. In some examples, a basal metabolic rate and active metabolism may be tracked as separate metrics. In certain embodiments, the metabolic rate may be calculated by DAM 113 based on one or more of inputs 127, such as one or more of activity information, sensor input, time, user input, etc.

In certain embodiments, the activity level metric may indicate the user's level of activity. In certain embodiments, the activity level metric be determined, for example, based on input from an activity sensor or other physiologic sensors. In certain embodiments, the activity level metric may be calculated by DAM 113 based on one or more of inputs 127, such as one or more of activity information, sensor input, time, user input, etc.

In certain embodiments, the insulin sensitivity metric may be determined using historical data, real-time data, or a combination thereof, and may, for example, be based upon one or more inputs 127, such as one or more of food consumption information, blood glucose information, insulin delivery information, the resulting glucose levels, etc. In certain embodiments, the insulin on board metric may be determined using insulin delivery information, and/or known or learned (e.g., from patient data) insulin time action profiles, which may account for both basal metabolic rate (e.g., update of insulin to maintain operation of the body) and insulin usage driven by activity or food consumption.

In certain embodiments, the meal state metric may indicate the state the user is in with respect to food consumption. For example, the meal state may indicate whether the user is in one of a fasting state, pre-meal state, eating state, post-meal response state, or stable state. In certain embodiments, the meal state may also indicate nourishment on board, e.g., meals, snacks, or beverages consumed, and may be determined, for example from food consumption information, time of meal information, and/or digestive rate information, which may be correlated to food type, quantity, and/or sequence (e.g., which food/beverage was eaten first.).

In certain embodiments, health and sickness metrics may be determined, for example, based on one or more of user input (e.g., pregnancy information or known sickness information), from physiologic sensors (e.g., temperature), activity sensors, or a combination thereof. In certain embodiments, based on the values of the health and sickness metrics, for example, the user's state may be defined as being one or more of healthy, ill, rested, or exhausted.

In certain embodiments, glucose level metrics may be determined from sensor information (e.g., blood glucose information obtained from glucose monitoring system 104). In some examples, a glucose level metric may also be determined, for example, based upon historical information about glucose levels in particular situations, e.g., given a combination of food consumption, insulin, and/or activity.

In certain embodiments, metrics 130 also include a disease stage, such as for Type II diabetics. Example disease stages for Type II diabetics can include a prediabetic stage, an oral treatment stage, and a basal insulin treatment stage. In certain embodiments, a degree of glycemic control (not shown) may also be determined as a metric, and may be based, for example, on one or more of glucose levels, variation in glucose level, or insulin dosing patterns.

In certain embodiments, clinical metrics generally indicate the clinical state the user is in with respect to the user's one or more conditions, such as diabetes. For example, in the case of diabetes, clinical metrics may be determined based on glycemic measurements, including one or more of A1c, trends in A1c, time in range, time spent below a threshold level, time spent above a threshold level, and/or other metrics derived from blood glucose values. In certain embodiments, clinical metrics may also include one or more of estimated A1c, glycemic variability, hypoglycemia, and/or health indicator (time magnitude out of target zone).

In certain embodiments, metrics 130 also include behavioral metrics which may include meal habits, disease treatment adherence, medication type and adherence, exercise regimen, etc. As further described below, in certain embodiments, DAM 113 may use historical records of the user's behavioral metrics to develop trends, based on which future behaviors of the user may be predicted. In certain embodiments, meal habits are measured by one or more metrics based on the content and the timing of the user's meals. For example, if the meal habit metric is on a scale of 0 to 1, the better/healthier meals the user eats the higher the meal habit metric of the user will be to 1, in an example. Also, the more the user's food consumption adheres to a certain time schedule, the closer their meal habit metric will be to 1, in the example. In certain embodiments, disease treatment and adherence are measured by one or more metrics that are indicative of how committed the user is towards treating the user's disease.

In certain embodiments, disease treatment and adherence metrics are calculated based on one or more of the user's diet or food consumption, exercise regimen, medication adherence, etc. In certain embodiments, medication adherence is measured by one or more metrics that are indicative of how committed the user is towards their medication regimen. In certain embodiments, medication adherence metrics are calculated based on one or more of the timing of when the user takes medication (e.g., whether the user is on time or on schedule), the type of medication (e.g., is the user taking the right type of medication), and the dosage of the medication (e.g., is the user taking the right dosage).

In certain embodiments, exercise regimen is measured by one or more metrics that are indicative of one or more of what type of activities the user engages in, how intense the activities are, how often the user engages in such activities, etc. In certain embodiments, the exercise regimen metrics may be calculated based on one or more activity sensors, calendar input, user input, etc.

In certain embodiments, inputs 127 and metrics 130 are timestamped to create a record of historical data for the user. Based on this record of historical data, DAM 113 is able to determine correlations between the different inputs 127, between the different metrics 130, and/or between inputs 127 and metrics 130. For example, based on the historical data, a correlation between the user's menstrual cycle and the user's blood glucose levels at different phases of the menstrual cycle may be determined. As one of ordinary skill in the art can appreciate, correlations between a variety of inputs 127 and/or metrics 130 may similarly be determined. For example, correlations between the dosage of administered insulin, the blood glucose levels, and different phases of the menstrual cycle may be determined. In certain embodiments, based on the record of historical data and/or the determined correlations, DAM 113 is then able to predict the user's change in insulin resistance and blood glucose levels during the different phases of the menstrual cycle as well as the predicted impact of different dosages of basal and bolus insulin, exercise, and food consumption on glucose levels during the different phases of the menstrual cycle. In certain embodiments, based on such predictions, the different features of application 106 are then able to recommend different treatments, such as different dosages of basal and/or bolus insulin, certain types and/or lengths of exercise, and certain types and/or portions of food.

Figure 3:
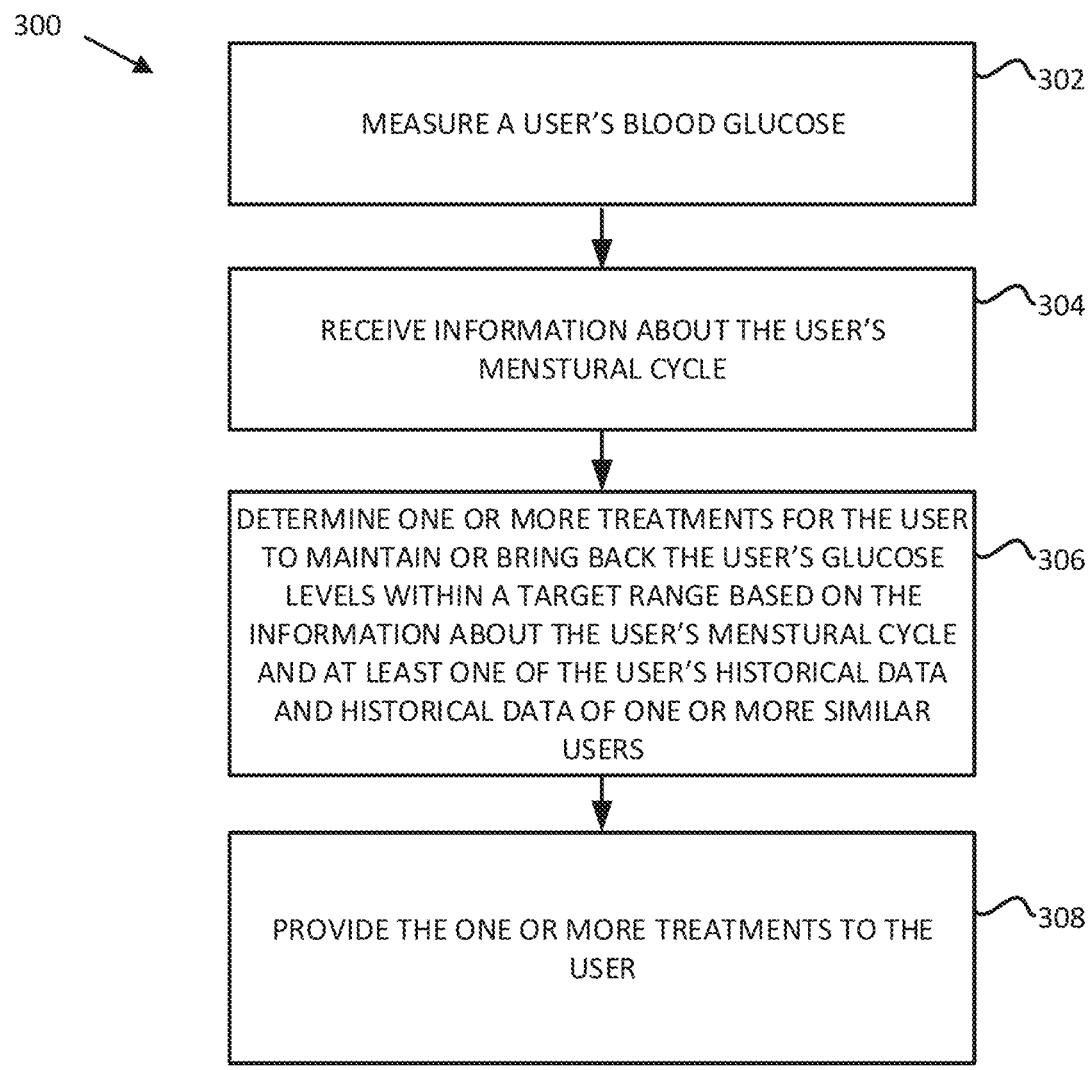
FIG. 3 is a flow diagram illustrating example operations performed by a system, such as the DSTA of FIG. 1A, according to some embodiments disclosed herein.

FIG. 3 is a flow diagram illustrating example operations 300 performed by a system (e.g., DSTA 100) for providing one or more treatments to a user based on where the user is in her menstrual cycle. The one or more treatments are determined based on information relating to a user and/or information relating to a pool of users, such as a stratified group of users that are similar in one or more aspects to the user. Operations 300 are described below with reference to FIGS. 1A-1B and 2 and their components. Note that the steps of operations 300 may not necessarily be performed in the order described herein. Furthermore, some steps herein may be omitted, and/or additional states may be added.

At step 302, operations 300 begin by measuring blood glucose of the user. In certain embodiments, step 302 is performed by glucose monitoring system 104. In certain embodiments, glucose monitoring system 104 is a continuous glucose monitoring system such that it is able to periodically (e.g., every 5 minutes) measure the user's blood glucose level. In certain embodiments, the glucose measurements are received and recorded by application 106 over time such that a record of the glucose measurements can be created. In certain embodiments, the record indicates all the past glucose measurements, including the most recent glucose measurement, which is considered to the user's real-time glucose measurement. Note that, in certain embodiments, application 106 is able to receive glucose measurements from glucose monitoring system 104 because, prior to using glucose monitoring system 104, the user goes through a set up process with application 106 to ensure that application 106 and glucose monitoring system 104 are able to identify each other and securely communicate. In certain embodiments, it is during the set up process or early phases of using application 106 that the user provides application 106 with at least one of her demographic information 118, disease progression information 120, and medication information 122.

At step 304, operations 300 continue by receiving information about the user's menstrual cycle, in some embodiments. In certain embodiments, step 302 is performed by DAM 113. For example, DAM 113 may receive information about the user's menstrual cycle as part of inputs 127. As described above, in certain embodiments, the information may be received from a third party software application that tracks, in real-time, where the user is in her menstrual cycle and is able to determine how long each phase lasts and when each phase is going to begin, etc. Such a software application may execute on mobile device 107 or on some other computing device that is in communication with mobile device 107 and/or DAM 113 over a network. In certain embodiments, as described above, DAM 113 may receive information about the user's menstrual cycle in the form of manual user input. For example, the user may input information about when their menstruation begins and ends as well as any additional information the user may have about their menstrual cycle.

At step 306, operations 300 continue by determining one or more treatments for the user to maintain or bring back the user's glucose levels within a target range based on the information about the user's menstrual cycle and at least one of the user's historical data and historical data associated with a stratified group of similar users. In certain embodiments, step 306 may be performed by DAM 113.

In certain embodiments, DAM 113 bases its determination of the one or more treatments on a number of data points that are either indicated by or calculated (e.g., predicted) based on the user's historical data and/or historical data associated with a stratified group of similar users. More specifically, in certain embodiments, DAM 113 may base its determination of the one or more treatments on what the user's glucose level and/or insulin resistivity are currently and/or will be at a certain time in the future (e.g., during different phases of the menstrual cycle). Further, in certain embodiments, DAM 113 may base its determination of the one or more treatments on information about treatments that have been effective in the past (e.g., past days, months, years) in maintaining or bringing the user's glucose levels back in the target range and/or treatments that have been effective in the past in maintaining or bringing glucose levels of one or more users in the stratified group back in the target range. Note that, a target range may refer to or include a target glucose level (e.g., a specific measurement).

As an example, a user's glucose level may currently be higher than a target glucose level. In such an example, DAM 113 may base its determination of the one or more treatments at least on the user's current glucose level, the difference between the current glucose level and the target glucose level, and/or the user's current insulin resistivity. The user's current insulin resistivity in this case is either calculated in real-time or based on the user's own historical data and/or historical data of associated with the stratified group. For example, in certain embodiments, the user's current insulin resistivity may be based on where the user is in their menstrual cycle and/or how insulin resistant the user has previously become during the same time period in the user's past menstrual cycles.

In another example, DAM 113 may determine one or more treatments to help the user maintain or achieve a certain glucose level at some point in the future. In such an example, DAM 113 may base its determination of the one or more treatments at least on the user's future glucose levels and/or insulin resistivity, which may be predicted based on the user's record of historical data and/or a record of historical data of one or more users in the stratified group. As an example, the user may be two days away from entering the luteal phase. In such an example, DAM 113 may anticipate this event, predict how insulin resistance the user will be during the luteal phase, and determine one or more treatments that have been effective in the past in helping the user achieve a certain glucose level during her luteal phase. As an example, in a simplified case, DAM 113 may determine that administering a certain dosage of basal insulin two days prior to the user entering her luteal phase is effective in maintaining the user's glucose level in the target range, for example, provided that the user continues to follow the same dietary and exercise regimens.

In certain embodiments, when the user begins using application 106, not enough inputs 127 and metrics 130 may be available about them. As such, in certain embodiments, conclusions with a high degree of confidence cannot be made about how the user's glucose levels fluctuate and/or how insulin resistant the user becomes in response to the user's hormonal changes during the different phases of the menstrual cycle. Similarly, in such embodiments, conclusions with a high degree of confidence cannot be made about what treatments are or can be effective in maintaining or bringing back the user's glucose levels in range during the different phases of the menstrual cycle. In certain embodiments, to be able to make confident conclusions based on the user's own historical data, at least a few months of inputs 127 and metrics 130 (e.g., one or more months) should be available for the user, although not necessary. As such, at least initially, DAM 113 may use historical data of one or more users in user database 110 in order to make predictions about how the user's glucose levels fluctuate and/or how insulin resistant the user becomes in the different phases of the menstrual cycle as well as what treatments are or can be effective during such phases.

In certain embodiments, DAM 113 may utilize historical data of all users in user database 110 in order to make the predictions described above. However, in certain other embodiments, DAM 113 may first stratify the user database 110 based on one or more similarity or stratification factors. In certain embodiments, depending on what data models and analyses are used, predictions made based on a dataset of a stratified group of similar users may be more accurate than predictions made based on a dataset associated with all users in user database 110.

A stratified group of users refers to a group of users in user database 110 that are similar to the user in one or more aspects. For example, when the user first begins using application 106, certain information may be determined about the user. Such information may include the user's demographic info 118, disease progression info 120, and/or medication info 122. As part of inputs 127, application 106 may also initially receive inputs about the user's menstrual information. As described above, all these inputs may be recorded in user profile 116. As such, DAM 113 may retrieve user profile 116 from user database 110 and select a stratified group of users from user database 110 based on one or more similarities between the information in user profile 116 and user profiles of a pool of users in user database 110. For example, DAM 113 may use one or more similarity or stratification factors for the stratification, the one or more stratification factors including at least one of the user's disease progression info, medication info, demographic info, menstrual cycle info, and/or any other additional data available in user profile 116 (e.g., inputs 127 and metrics 130, if available).

One of a variety of methods and approaches may be used for stratifying user database 110 based on one or more stratification factors (e.g., disease progression, medication info, demographic information, objectives, menstrual cycle, inputs 127, metric 130, or a combination thereof). In certain embodiments, DAM 113 may use one of a variety of data filtering techniques to filter the broader user database 110 based on one or more stratification factors. For instance, if the user has Type I diabetes, DAM 113 may filter all user profiles in user database 110 who also have Type I diabetes. In that case, the stratified group of user would include all such users. In certain embodiments, however, if additional stratification factors are used for stratification, then additional filtering may be performed to further narrow the group of users in the stratified group. For example, if the stratification factors include disease progression and demographic info and the user is a female who has Type I diabetes, then DAM 113 may filter all user profiles of all female users in user database 110 who also have Type I diabetes.

In certain embodiments, DAM 113 may use machine learning algorithms to stratify user database 110. For instance, an unsupervised learning algorithm may be used for clustering all user profiles in user database 110 and determining to which cluster user profile 116 belongs. Unsupervised learning is a type of machine learning algorithm used to draw inferences from datasets consisting of input data without labeled responses. As one of ordinary skill in the art appreciates, in addition to an unsupervised learning algorithm that focuses on a clustering analysis, other types of unsupervised learning algorithms may be used.

In certain embodiments, a supervised learning algorithm may be used instead. Supervised learning is the machine learning task of learning a function that, for example, maps an input to an output based on example input-output pairs. In certain embodiments, using a supervised learning algorithm, DAM 113 may be configured to classify user profile 116 by determining what class or stratified group of users the user belongs to, based on a machine learning model that has been trained using a labeled dataset. In certain embodiments, the labeled data already includes different classes of users that are classified based on one or more characteristics, such as disease progression. For instance, in certain embodiments, one class of users includes all user profiles with females in the age range of 25-27, while another class of users includes all females within the age range of 27-29. In such an example, if demographic info 118 of user profile 116 indicates that the user is 26 years old, then DAM 113 selects the first class as the stratified group of users (if the only stratification factor is age).

In some embodiments, when selecting a stratified group of users, DAM 113 may be configured to define a range around each of the stratification factors. As an example, if the user is 25 years old, a range of four years may be defined such that all users within the age range of 23-27 would be included in the stratified group.

Once a group of users is selected from user database 110, whether the group corresponds to all the users in user database 110 or users in the stratified group, DAM 113 uses a record of historical data associated with such a group to make predictions about the user's glucose level and/or insulin resistivity based on the user's menstrual cycle (e.g., during different phases of the menstrual cycle).

As an example, when the user initially uses application 106, user profile 116 may indicate that the user is a 25 year old Caucasian female, who is Type I and injects insulin. User profile 116 may also indicate details about the user's menstrual cycle. In such an example, DAM 113 may stratify user database 110 based on one or more of the stratification factors described above. For example, DAM 113 may stratify user database 110 to find a dataset associated with all Caucasian female users within the age range of 24-26 who have Type I diabetes and inject insulin. Note that DAM 113 may or may not use the user's menstrual cycle information as a stratification factor.

In certain embodiments, DAM 113 may then examine the dataset to make predictions about the user's glucose levels and insulin resistivity during a certain point in the user's menstrual cycle. For example, the user may be 2 days away from entering her luteal phase. In such an example, DAM 113 anticipates this based on the user's menstrual cycle information. As information about how insulin resistant the user may become during her luteal phase or certain sub-phases of the luteal phase (or other phases and/or sub-phases of the menstrual cycle) may still not be available, in certain embodiments, DAM 113 then examines the dataset associated with the stratified group of users to determine, on average, how insulin resistant the users in the stratified group become during the various phases and/or sub-phases of their menstrual cycles (e.g., luteal phases).

In certain embodiments, the user's luteal phase (or any other phase in the menstrual cycle) may be divided into various sub-phases, where each sub-phase may correspond to a certain range of time in the luteal phase. As an example, the luteal phase of the user may include sub-phases such as a beginning sub-phase, a middle sub-phase, and an end sub-phase. In another example, the sub-phases may correspond to the number of days, such as if the luteal phase of the user is normally seven days, then seven sub-phases may be defined. Sub-phases may also corresponded to hours and minutes, such that, for example, the first sub-phase of the luteal phase may correspond to the first hour of the luteal phase. Because insulin resistivity varies by different amounts at different times during the luteal phase, in certain embodiments, dividing the luteal phase into sub-phases help with more accurately determining how insulin resistant users in the stratified group are during specific time periods, based on which the user's insulin resistivity and/or glucose levels can be predicted.

When the luteal phase is divided into sub-phases for all users, DAM 113 is able to determine what the average change in insulin resistance is for a stratified group of users during the same certain sub-phase that the user is in or will be entering. For example, if the user is 2 days away from entering the luteal phase, that may mean that the user is 2 days away from entering the first sub-phase of the luteal phase, where the first sub-phase corresponds to the beginning phase, the first day, or some other convention that DAM 113 may be configured with.

As such, in certain embodiments, DAM 113 examines the dataset associated with the stratified group to determine how insulin resistant such users become on average and/or by how much such users' glucose levels vary during their first luteal sub-phase. Based on that information, in certain embodiments, DAM 113 is able to predict how insulin resistant the user will be and/or by how much the user's glucose levels will vary in her first sub-phase if the user does not incorporate any additional treatments (e.g., additional exercise, a more restrictive diet, additional dosage of basal and/or bolus insulin).

Note that, although certain embodiments herein describe changes in insulin resistance during the luteal phase, a user's insulin resistance may vary during other phases of the menstrual cycle. As such the embodiments described herein are similarly applicable to other phases or sub-phases of the menstrual cycle. In other words, the luteal phase is used merely as an example.

Also, note that, in certain embodiments, instead of or in addition to examining the dataset associated with the stratified group, DAM 113 may consider scientific data points that indicate by how much, on average, the user's insulin resistivity and/or glucose levels may change during certain phases and/or sub-phases of the user's menstrual cycle. For example, in certain embodiments, such scientific data points may be backed by scientific research and be provided to DAM 113 as a dataset that indicates how (e.g., by how much) different users with different characteristics (e.g., demographic info, disease progression, medication info, menstrual cycle info, etc.) may experience a change in insulin resistivity and/or glucose levels during different sub-phases and/or phases of their menstrual cycles. As an example, in such cases, a rule-based approach may be used such that, for example, if the user is 25 years old, a rule may indicate that, based on the scientific data points, the user's insulin resistance will increase by 30% during the first sub-phase of a certain phase in the user's menstrual cycle (e.g., the luteal phase), because females with that age generally experience that much increase in insulin resistance. The scientific data points may indicate the change in insulin resistivity for each sub-phase and/or phase of the menstrual phase. For example, the data may indicate that the user's insulin resistance will increase by 40% during the second sub-phase.

In certain embodiments, predicting how insulin resistant the user may be and/or by how much the user's glucose levels may potentially vary in the first sub-phase may help DAM 113 also predict one or more treatments for the user to maintain her glucose levels in a target range when she enters the first sub-phase. For example, DAM 113 may be configured with scientific data points that indicate certain type or amounts of treatment that may help maintain the user's glucose levels within a certain range even in light of the change in insulin resistivity during a certain phase or sub-phase. For example, certain scientific data points may indicate that for a 25 year old user, on average, administering an extra 20% of basal insulin, a certain amount of time prior to the first sub-phase or at certain point in time during the first sub-phase, has shown to be effective in counteracting the 30% increase in insulin resistivity during a certain sub-phase or phase of the menstrual cycle. In another example, the scientific data points may indicate that an additional 1 hour of exercise on a daily basis has shown to be effective in counteracting a 10% increase in insulin resistivity during a certain sub-phase or phase of the menstrual cycle. In another example, the scientific data points may indicate that following a more restrictive diet (e.g., less carbs, etc.) on a daily basis has shown to be effective in counteracting a 15% increase in insulin resistivity during a certain sub-phase or phase of the menstrual cycle.

Note that these are simplified examples to illustrate how data points, based on scientific research, can be used in recommending treatments to the user. As such, these simplified examples are not meant to limit the scope of the disclosure. In certain embodiments, when scientific data points are used, DAM 113 may be configured with a rule-based approach such that, for example, if the user's increase in insulin resistivity is 20% during the first sub-phase and the scientific data points suggest that an additional dosage of insulin is able to counteract a 10% increase in insulin resistivity, DAM 113 may be configured to recommend double that dosage to the user. In another example, instead, DAM 113 may be configured to recommend the same additional dosage to counteract 10% of the increase and an additional 1 hour of daily exercise to counteract the other 10% increase in insulin resistivity, etc. As such, a combination of treatments (e.g., insulin, dietary restriction, exercise) may also be recommended.

In certain embodiments, instead of or in addition to determining one or more treatments based on examining the scientific data points described above, DAM 113 may predict what one or more treatments may be effective to counteract the change in the user's insulin resistivity during a sub-phase or a phase of the user's menstrual cycle, based on the dataset associated with the stratified group. Note that, as described above, the dataset, in certain embodiments, may correspond to the entire pool of users and not a stratified pool of users. In other words, predictions may similarly be made with respect to effective treatments based on data associated with all users; stratifying user database 110 is, therefore, not necessary. One of ordinary skill in the art can appreciate the various methods and operations that may be utilized to make such predictions based on the dataset associated with the stratified group of users.

For example, one or more data model(s), machine learning model(s), regression model(s), function(s), and algorithm(s) may be used, in certain embodiments, to predict one or more treatments or a combination thereof to counteract a certain amount of change in insulin resistivity during a certain sub-phase or phase of the menstrual cycle. A few examples of different algorithms that may be used are described in relation to FIG. 4.

Figure 4:
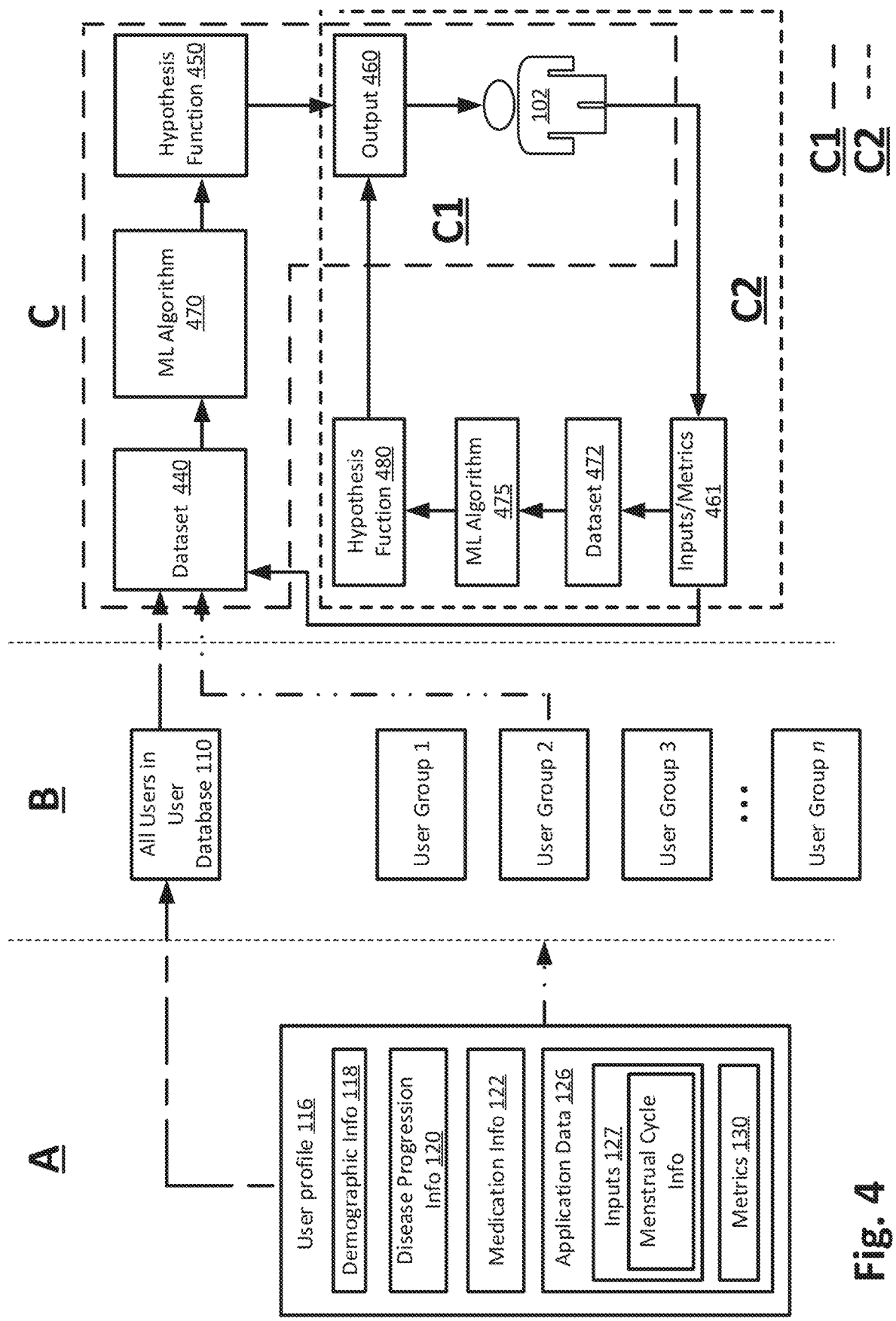
FIG. 4 is a diagram illustrative of one example of how one or more treatments are determined for the user, in accordance with certain embodiments.

In certain embodiments, these data model(s), machine learning model(s), regression model(s), function(s), or algorithm(s) may be used to find correlations between the different variables (e.g., data features, as described in more detail with respect to FIG. 4). In one example, one variable may be defined based on the menstrual sub-phase or phase. Another variable may be glucose levels, or a change therein. A number of other variables may also be defined, including a variable associated with an administered dosage of insulin, a variable associated the amount and/or type of exercise, a variable associated with the type and/or amount of consumed food.

In certain embodiments, based on these correlations, DAM 113 may be able to identify consistent patterns, based on which DAM 113 may be configured to predict effective treatments for the user. These patterns, in certain embodiments, show the impact of different types/amounts of medicine (e.g., insulin) as well as types/amounts of user actions (e.g., exercise, food) on the users' glucose levels, in different sub-phase/phases of the menstrual cycle.

For example, the dataset may indicate that on average, for female users in the age range of 24-26, administering an extra 20% of basal insulin (e.g., a certain amount of time prior to the first sub-phase or at a certain point in time during the first sub-phase) counteracted the 30% increase in insulin resistivity during the first sub-phase of the luteal phase. In another example, the dataset may indicate that, for Caucasian female users with Type 1 diabetes, an additional 1 hour of exercise on a daily basis counteracted a 10% increase in insulin resistivity during a certain sub-phase or phase of the menstrual cycle. In yet another example, the dataset may indicate that, for female users with the same exact menstrual cycle as the user, following a more restrictive diet (e.g., less carbs, etc.) on a daily basis counteracted a 15% increase in insulin resistivity during a certain sub-phase or phase of the menstrual cycle. Note that these are simplified examples to illustrate how a dataset associated with a group of users can be used in recommending treatments to the user. As such, these simplified examples are not meant to limit the scope of the disclosure. Based on these consistent patterns, DAM 113 may then predict what one or more treatments may be helpful to the user.

In certain embodiments, as additional inputs 127 and metrics 130 are received and stored in user profile 116 over time, a dataset associated with the user's own historical data may be developed, based on which DAM 113 may determine one or more treatments to help the user maintain or reach a certain glucose range based on where the user is in her menstrual cycle. For example, the additional inputs 127 and metrics 130 may include information about the different treatments provided to the user based on the dataset associated with the stratified group of users (or the entire user group in user database 110) and/or the scientific data points. The additional inputs 127 and metrics 130 may also include information about the impact such treatments had on the user, such as the impact on the user's physiology (e.g., glucose levels, etc.).

In certain embodiments, the user's own historical data may provide even more accurate predictions as to what the user's glucose level and/or insulin resistance is or will be in a certain sub-phase or phase of the menstrual cycle as well what one or more treatments will be effective during such sub-phase or phase. One of ordinary skill in the art can appreciate the various methods and operations that may be utilized to make such predictions based on the dataset associated with the user herself.

For example, one or more data model(s), machine learning model(s), regression model(s), function(s), and algorithm(s) may be used, in certain embodiments, to predict one or more treatments or a combination thereof to counteract a certain amount of change in insulin resistivity during a certain sub-phase or phase of the menstrual cycle. A few examples of different algorithms that may be used are described in relation to FIG. 4. In certain embodiments, these data model(s), machine learning model(s), regression model(s), function(s), or algorithm(s) may be used to find correlations between the different variables (e.g., features). As described above, the variables may include glucose levels, and/or changes therein, insulin resistance, and/or changes therein, the menstrual sub-phase or phase, as well as exercise and food related variables.

In certain embodiments, based on these correlations, DAM 113 may be able to identify consistent patterns, based on which DAM 113 may be configured to determine effective treatments for the user. These patterns, in certain embodiments, show the impact of different types/amounts of medicine (e.g., insulin) as well as types/amounts of user behavior (e.g., exercise, food) on the user's glucose levels, in different phases of the menstrual cycle.

For example, the dataset may indicate that, over the past 12 months, on average, administering an extra 40% of basal insulin counteracted the user's 30% increase in insulin resistivity during a certain sub-phase or phase of the menstrual cycle. In another example, the dataset may indicate that an additional 1 hour of exercise on a daily basis was not enough to counteract a 10% increase in insulin resistivity during a certain sub-phase or phase of the menstrual cycle. Similar examples are also within the scope of the disclosure. Based on the user's own historical data and the patterns found therein, DAM 113 is then able to determine what one or more treatments are or are not effective.

At step 306, operations 300 continue by providing the one or more treatments to the user. The one or more treatments, as described above, may have been determined based on historical data associated with the user, historical data associated with one or more users in user database 110, and/or scientific data points.

In certain embodiments, if the one or more treatments include administering a certain dosage of insulin, then once a certain dosage of insulin has been determined by DAM 113, the medication management feature of application 106 may send a therapy recommendation (e.g., notification) to the user with the delivery dosage and/or time of delivery so that the user can manually administer the insulin. Alternatively, the medication management feature may (e.g., upon receiving the user's approval) automatically communicate with an insulin administration device to deliver the determined dosage at the delivery time. In certain embodiments, when the user only consumes insulin in the form of oral medication, then a treatment may indicate an effective dosage of such oral insulin. Providing the right dosage of insulin, to be automatically or manually administered, is advantageous because, otherwise, the user may either (1) overcompensate by administer an excessive amount of insulin to counteract her change in insulin sensitivity, or (2) administer too little insulin and see a spike in her glucose levels, which may cause the user to keep injecting additional dosages.

In certain embodiments, if the one or more treatments include exercising more and/or differently during a certain sub-phase or phase, then the exercise management feature provides a therapy recommendation including the type and/or intensity of the exercise to the user. For example, the dataset associated with the user's historical data may show that an hour of running during the user's luteal phase consistently resulted in helping the user maintain her glucose levels within a target range. In such an example, the exercise management feature suggests an hour of additional running or an exercise with a similar type and/or intensity (swimming) to the user. The exercise management feature may, for example, calculate that if the user were to swim instead of run, then 45 minutes of swimming would be enough.

In certain embodiments, if the one or more treatments include a change in diet during a certain sub-phase or phase, then the diet management feature may provide a therapy recommendation including the different ways and forms the user could conform their diet accordingly. For example, the dataset associated with the user's historical data may show that consuming fewer than 15 grams of sugar or 50 grams of carbs during the user's luteal phase consistently resulted in helping the user maintain her glucose levels within a target range. In such an example, the diet management feature may recommend such a finding to the user as a treatment and also recommend diets with meals and dishes that will conform to what has been effective in the past.

In certain embodiments, a combination of the two or more treatments may be recommended to the user. For example, certain users may generally like to be less dependent on insulin, for different reasons, in which case, to counteract their insulin resistivity, application 106 may recommend a combination of exercise and diet. Such a combination, which may exclude the administration of insulin, may be determined based on the user's own historical data and/or historical data associated with one or more users in user database 110. For example, the user may have always only administered additional insulin to counteract her change in insulin resistance during a certain phase of the menstrual cycle, e.g., the luteal phase. However, the user may instead decide to do additional exercises and follow a more restrictive diet during her luteal phase instead of administering additional insulin. In such a case, the user's own historical data may not show strong support for how the user's glucose levels react to more exercise and/or a more restrictive diet during her luteal phase. In such an example, inferences are drawing from historical data of similar users, which may show that a certain additional amount of exercise and/or a certain change in diet may be effective.

FIG. 4 is a diagram illustrative of one example of how one or more treatments are determined for the user, in accordance with certain embodiments. As shown, in the example of FIG. 4, data is gathered and prepared in three steps of A, B, and C (including steps C1 and C2). In step A, application 106 receives certain initial inputs from or about the user, such as demographic information 118, disease progression information 120, medication information 122, inputs 127 (including the menstrual cycle information) and/or metrics 130. As described above, because initially not enough inputs 127 and metrics 130 may have been received and/or are available for the user, in the example of FIG. 4, DAM 113 initially, in step C1, determines one or more treatments for the user based on a dataset 440 associated with one or more users in user database 110.

Dataset 440 may correspond to a record of historical data associated with all users in user database 110 or a stratified group of users. These alternatives are shown with different types of dashed lines. For example, in certain embodiments, in step B, DAM 113 stratifies user database 110 based on one or more stratification factors, as described above, which results in a stratified group of users, shown as User Group 2. In such embodiments, dataset 440 corresponds to a record of historical data associated with User Group 2. In certain other embodiments, in step B, DAM 113 may determine not to stratify user database 110, in which case dataset 440 corresponds to a record of historical data associated with all users in user database 110.

In step C1, in certain embodiments, dataset 440 is used as a training dataset that is fed into machine learning (ML) algorithm 470 to output a hypothesis function 450 (i.e., h). As described above, dataset 440 is developed and recorded such that it includes a variety of data features (DFs), such as: one or more DFs corresponding to time and/or where (e.g., what sub-phase or phase) the user is in their menstrual cycle, one or more DFs corresponding to blood glucose levels and/or change therein, one or more DFs corresponding to insulin resistance and/or change therein, one or more exercise-related DFs corresponding to type and amount of exercises performed, one or more diet-related DFs corresponding to dietary restrictions and/or the type and amount of food consumed, one or more DFs corresponding to type and/or amount of administered insulin, and/or additional DFs that may be used for this model, as one of ordinary in the art appreciates. For example, any of the inputs and metrics (e.g., inputs 127 and metrics 130) may be used for defining additional DFs. Note that, in machine learning and pattern recognition, a DF is an individual measurable property or characteristic of a phenomenon being observed. In certain embodiments, ML algorithm 470 is a supervised learning algorithm. Supervised learning is the machine learning task of learning a function that, for example, maps an input to an output based on example input-output pairs. In the example of FIG. 4, ML algorithm 470 may include supervised learning algorithm for solving a multivariable or multivariate regression problem.

As described above, feeding dataset 440 into ML algorithm 470 results in a hypothesis function 450, which takes as input one or more x's and maps them to a y. Hypothesis function 450 is developed based on correlations between the different DFs in dataset 440. For example, hypothesis function 450 may correspond to the function below, where Y is a dependent variable while X1, X2, . . . , Xp are various independent variables.

$$Y = \beta 0 + \beta 1 X1 + \beta 2 X2 + \beta X3 + \ldots + \beta p Xp + \epsilon.$$

In certain embodiments, each of the independent variables corresponds to a different DF. For example, Y may correspond to a glucose level (e.g., or a reduction in glucose level, or a target glucose level or range), X1 may correspond to time and/or where (e.g., what sub-phase or phase) the user is in their menstrual cycle, X2 may be diet related, X3 may correspond to a type and/or amount of exercises performed, X4 may correspond to a type and/or amount of administered insulin, X5 may relate to insulin resistance, and so on. B0, B1, . . . , Bp are coefficients that, in certain embodiments, represent correlations between corresponding Xs and Y. Note that choosing glucose level as Y, or the output, is only one way of arranging hypothesis function 450. Details of how hypothesis function 450 is outputted and constantly tailored by ML algorithm 470 based on dataset 440 (such as, potentially, the use of a cost function, gradient descent algorithm, etc.) is not described herein for brevity but is known to one of ordinary skill in the art.

Using hypothesis 450, in certain embodiments, DAM 113 is able to predict the user's glucose level, given a specific sub-phase, phase, or point in time during the user's menstrual cycle, the amount type of exercise, the amount/type of food, and/or the amount/type of administered insulin. Using hypothesis 450, DAM 113 is also able to determine one or more treatments for the user. To illustrate this with an example, the user may be 2 days away from entering the first sub-phase of the luteal phase. The user may have indicated that the user would not like to engage in any additional exercise or follow any additionally restrictive diet. In that example, DAM 113 may use a target glucose range or level in hypothesis function 450 as "Y," and determine the amount of insulin "X4" that needs to be administered during that sub-phase, given "X1" having a value that represents the first sub-phase of the luteal phase, and given the same values for X2 and X3 (e.g., values representing the same exercise and food regimen). In another example, the amount of administered insulin may stay the same while DAM 113 determines how much additional exercise the user needs to engage in during the first sub-phase to reach that target glucose level. There are numerous ways hypothesis function 450 can be arranged and used, as one of ordinary skill in the art can appreciate. For example, individual treatments or a combination of treatments may be determined based on hypothesis function 450. In another example, 'Y' may represent the reduction in glucose levels. In such an example, DAM 113 may use hypothesis function 450 to predict what one or more treatments may result in a certain amount of reduction in glucose level.

Note that although the development of hypothesis 450 is shown in step C1 of FIG. 4, hypothesis 450 may be developed by DAM 113 based on dataset 440 even prior to the user using application 106 (e.g., prior to step A). In other words, DAM 113 may use datasets associated with different stratified groups to develop functions that can then be used when a new user starts using application 106 and is in need of treatment recommendations. For example, a different hypothesis function may be developed for User Group 3 such that if a new user starts utilizing application 106 and falls into User Group 3, then DAM 113 is able to utilize that hypothesis function to predict what one or more treatments may be effective for the user during a certain sub-phase, phase, or point in time of the user's menstrual cycle.

Utilizing a supervised learning algorithm to develop a function such as hypothesis function 450 is only one example of how DAM 113 may predict the user's glucose levels during a certain sub-phase or phase of the menstrual cycle and/or predict one or more effective treatments for that sub-phase or phase to help the user maintain or reach a certain glucose level or range. Other machine learning algorithms, such as a neural network algorithm, may instead be used.

Output 460 represents the one or more treatments that may be recommended to or administered to the user. The physiological impact output 460 has on the user (e.g., shown as user 102) is then received and recorded in the form of inputs/metrics 461 by application 106. For example, output 460 may include an administration of a certain dosage of basal insulin a day prior to the user entering the first sub-phase of the luteal phase. In such an example, when the user enters the first sub-phase, her glucose level may be higher than desired. The user's glucose level and other metrics, in that example, are then received, recorded, and analyzed as inputs/metrics 461. Inputs/metrics 461 are not only recorded in user profile 116, whose information is then fed hack to dataset 440, but they are also used to develop a training dataset 472 specifically for the user. Accordingly, output 460 and inputs/metrics 461 are used to develop both dataset 440 and dataset 472.

When additional inputs and metrics are fed back into dataset 440, an updated dataset 440 is again fed back into ML algorithm 470, thereby resulting in a constantly changing and dynamic hypothesis function 450 that is reflective of the updates to the data in dataset 440. A constantly changing and dynamic hypothesis function 450 refers to, among other things, a dynamic set of coefficients (e.g., B0, B1, . . . , Bp).

After a certain amount of time, dataset 472 may be developed enough such that, based on dataset 472, predictions with high degrees of confidence can be made about the user's glucose levels and/or insulin resistivity as well as how effective different treatments may be during a certain sub-phase or phase of the user's menstrual cycle. At such point in time, in step C2, in certain embodiments, DAM 113 may utilize predictions provided based on dataset 472 to provide treatments to the user or at least give more weight to such predictions in comparison to predictions provided based in dataset 440. Similar to dataset 440, dataset 472 may be used as a training dataset that can be fed into a machine learning algorithm 475 to develop a hypothesis function 480. A similar or a different type of machine learning algorithm 475 as with dataset 440 may be used, as one or ordinary skill in the art appreciates. For example, ML algorithm 475 may be a supervised learning regression algorithm. As such, based on the user's own historical data (dataset 472), the resulting hypothesis function 480, in certain embodiments, is used to predict the user's glucose levels and/or insulin resistance as well as one or more treatments that may be effective in helping the user maintain or achieve a certain glucose level during a certain sub-phase or phase of the user's menstrual cycle.

What is outputted by hypothesis function 480, in the form of treatment recommendations and/or treatment administration, in certain embodiments, is provided to the user as output 460. The physiological impact of such output 460, being performed or administered, is then received and/or recorded in the form of inputs/metrics 461 to further develop dataset 472. When additional inputs/metrics 461 are fed hack into dataset 472, an updated dataset 472 is again fed back into ML algorithm 475, thereby resulting in a constantly changing and dynamic hypothesis function 480 that is reflective of the dynamic updates to the data in dataset 472.

In certain embodiments, DAM 113 may determine one or more treatments for the user based on the outputs provided by both hypothesis functions 480 and 450. For example, in certain embodiments, DAM 113 may not have a high degree of confidence in the output provided by hypothesis function 480. As such, in such an example, DAM 113 may supplement the output provided by hypothesis function 480 with output provided by hypothesis function 450. For example, DAM 113 may use a function that provides a final output based on weights assigned to the output provided by hypothesis function 480 and the output provided by hypothesis function 450.

Note that using a combination of the historical data associated with the stratified group of users and the historical data associated with the user is only one example of how effective treatments can be predicted and provided to the user. In certain other embodiments, DAM 113 may initially only predict and provide treatments to the user based on scientific data points and then use the user's own historical data, when enough is available. In yet certain other embodiments, only the user's own data may be used because enough information may be available about the user from the beginning. As an example, the user may separately use application 106 and a third party period tracking application for a few years. In such an example, at some point the user may provide application 106 with access to the user's historical menstrual cycle information during the past few years by enabling application 106 to communicate with the third party period tracking application, which has that record. As such, in that example. DAM 113 may correspond the user's menstrual cycle information with the user's glucose and/or insulin resistance trends and created a time-stamped set of data that can then be fed into a machine learning algorithm and create a hypothesis function for predictions. In yet certain other embodiments, DAM 113 may only rely on the historical data associated with the stratified group of users to provide the user with effective treatments.

Figure 5:
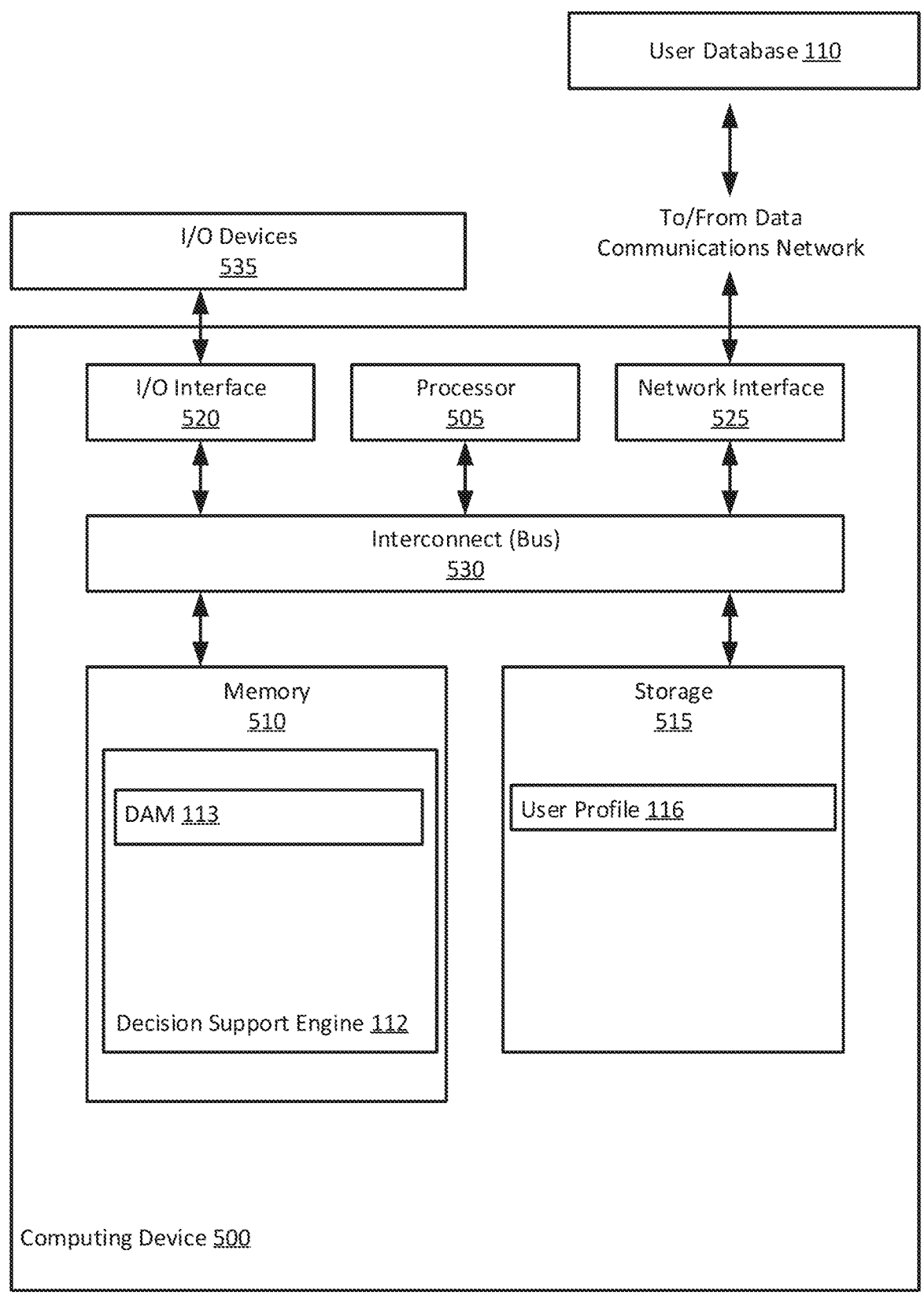
FIG. 5 is a block diagram depicting a computing device configured to perform one or more steps of the operations of FIG. 3, according to certain embodiments disclosed herein.

FIG. 5 is a block diagram depicting a computing device 500 configured to predict the user's glucose levels and/or insulin resistance as well as one or more treatments that may be effective in helping the user maintain or achieve a certain glucose level during a certain sub-phase or phase of the user's menstrual cycle. In certain embodiments, the one or more treatments are then provided by an application to the user, the application executing on either computing device 500 or another computing device in communication with computing device 500, according to certain embodiments disclosed herein. Although depicted as a single physical device, in embodiments, computing device 500 may be implemented using virtual device(s), and/or across a number of devices, such as in a cloud environment. As illustrated, computing device 500 includes a processor 505, memory 510, storage 515, a network interface 525, and one or more I/O interfaces 520. In the illustrated embodiment, processor 505 retrieves and executes programming instructions stored in memory 510, as well as stores and retrieves application data residing in storage 515. Processor 505 is generally representative of a single CPU and/or GPU, multiple CPUs and/or GPUs, a single CPU and/or GPU having multiple processing cores, and the like. Memory 510 is generally included to be representative of a random access memory. Storage 515 may be any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, input and output (I/O) devices 535 (such as keyboards, monitors, etc.) can be connected via the I/O interface(s) 520. Further, via network interface 525, computing device 500 can be communicatively coupled with one or more other devices and components, such as user database 110. In certain embodiments, computing device 500 is communicatively coupled with other devices via a network, which may include the Internet, local network(s), and the like. The network may include wired connections, wireless connections, or a combination of wired and wireless connections. As illustrated, processor 505, memory 510, storage 515, network interface(s) 525, and I/O interface(s) 520 are communicatively coupled by one or more interconnects 530. In certain embodiments, computing device 500 is representative of mobile device 107 associated with the user. In certain embodiments, as discussed above, the mobile device 107 can include the user's laptop, computer, smartphone, and the like. In another embodiment, computing device 500 is a server executing in a cloud environment.

In the illustrated embodiment, storage 515 includes user profile 116. In certain embodiments, storage 515 also includes any datasets that may be used in one or more operations described in relation to FIGS. 3 and 4. In certain other embodiments, such datasets may instead or additionally be stored in user database 110. Memory 510 includes decision support engine 112, which itself includes DAM 113. Decision support engine 112 is executed by computing device 500 to perform one or more steps of operations 300 in FIG. 3.

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system comprising:
a processor;
a glucose sensor configured to measure glucose levels of a user to generate glucose measurements;
a sensor electronics module configured to transmit sensor data corresponding to the glucose measurements provided by the glucose sensor to the processor; and
a memory circuit in communication with the processor,
wherein the processor is configured to execute instructions stored in the memory circuit to:
receive information relating to a menstrual cycle of the user, the menstrual cycle comprising a plurality of menstrual phases,
identify a menstrual phase from the plurality of menstrual phases that the user is currently in;
determine a treatment for the user to achieve a target glucose during the identified menstrual phase of the menstrual cycle of the user based on historical data associated with a stratified group of users, wherein the stratified group of users is stratified at least based on menstrual cycle information,
wherein the historical data associated with the stratified group of users is structured to indicate a change in insulin resistance associated with the stratified group of users historically being in the identified menstrual phase, and a pattern of physiological impact of a plurality of treatments including the determined treatment on glucose measurements of the stratified group of users during the identified menstrual phase, the pattern indicating effectiveness of the plurality of treatments in regards to counteracting the change in insulin resistance and achieving the target glucose, and
transmit a signal to an insulin delivery device, thereby causing the insulin delivery device to administer insulin to the user based on the determined treatment.

2. The system of claim 1, wherein the determined treatment comprises a dosage of insulin.

3. The system of claim 2, wherein the dosage of insulin is higher than an average dosage of insulin administered to the user during non-luteal menstrual phases of the menstrual cycle of the user.

4. The system of claim 1, wherein the determined treatment comprises a therapy recommendation and the processor is configured to provide the therapy recommendation.

5. The system of claim 4, wherein the therapy recommendation is indicative of a recommended dosage of insulin.

6. The system of claim 4, wherein the therapy recommendation is indicative of at least one of an amount, type, length, or intensity of exercise.

7. The system of claim 4, wherein the therapy recommendation is indicative of at least one of an amount or type of food.

8. The system of claim 1, wherein causing the insulin delivery device to administer insulin to the user comprises causing the insulin delivery device to administer the insulin to the user subsequent to the user approving the determined treatment.

9. A method of personalizing diabetes treatment based on a menstrual cycle of a user, comprising:
measuring, using a glucose monitoring system, glucose measurements of the user;
receiving, at a processor in data communication with the glucose monitoring system, information relating to the menstrual cycle of the user, the menstrual cycle comprising a plurality of menstrual phases;
identifying a menstrual phase from the plurality of menstrual phases that the user is currently in;
determining, at the processor, a treatment for the user to achieve a target glucose during the identified menstrual phase of the menstrual cycle of the user based on historical data associated with a stratified group of users, wherein the stratified group of users is stratified at least based on menstrual cycle information,
wherein the historical data associated with the stratified group of users is structured to indicate a change in insulin resistance associated with the stratified group of users historically being in the identified menstrual phase, and a pattern of physiological impact of a plurality of treatments including the determined treatment on glucose measurements of the stratified group of users during the identified menstrual phase, the pattern indicating effectiveness of the plurality of treatments in regards to counteracting the change in insulin resistance and achieving the target glucose; and
transmitting a signal to an insulin delivery device, thereby causing the insulin delivery device to administer insulin to the user based on the determined treatment.

10. The method of claim 9, wherein the determined treatment comprises a dosage of insulin.

11. The method of claim 10, wherein the dosage of insulin is higher than an average dosage of insulin administered to the user during non-luteal menstrual phases of the menstrual cycle of the user.

12. The method of claim 9, wherein the determined treatment comprises a therapy recommendation, the method further comprising providing the therapy recommendation.

13. The method of claim 12, wherein the therapy recommendation is indicative of a recommended dosage of insulin.

14. The method of claim 12, wherein the therapy recommendation is indicative of at least one of an amount, type, length, or intensity of exercise.

15. The method of claim 12, wherein the therapy recommendation is indicative of at least one of an amount or type of food.

16. The method of claim 9, wherein causing the insulin delivery device to administer insulin to the user comprises causing the insulin delivery device to administer the insulin to the user subsequent to the user approving the determined treatment.

17. A non-transitory computer readable medium having instructions stored thereon that, when executed by a system, causes the system to perform a method comprising:

measuring, using a glucose monitoring system, glucose measurements of a user;

receiving, at a processor in data communication with the glucose monitoring system, information relating to a menstrual cycle of the user, the menstrual cycle comprising a plurality of menstrual phases;

identifying, at the processor, a menstrual phase from the plurality of menstrual phases that the user is currently in;

determining, at the processor, a treatment for the user to achieve a target glucose during the identified menstrual phase of the menstrual cycle of the user based on historical data associated with a stratified group of users, wherein the stratified group of users is stratified at least based on menstrual cycle information, wherein the historical data associated with the stratified group of users is structured to indicate a change in insulin resistance associated with the stratified group of users historically being in the identified menstrual phase, and a pattern of physiological impact of a plurality of treatments including the determined treatment on glucose measurements of the stratified group of users during the identified menstrual phase, the pattern indicating effectiveness of the plurality of treatments in regards to counteracting the change in insulin resistance and achieving the target glucose; and transmitting a signal to an insulin delivery device, thereby causing the insulin delivery device to administer insulin to the user based on the determined treatment.

18. The non-transitory computer readable medium of claim 17, wherein the determined treatment comprises a therapy recommendation and the method further comprises providing the therapy recommendation.

19. The non-transitory computer readable medium of claim 17, wherein the determined treatment comprises a recommended dosage of insulin that is higher than an average dosage of insulin administered to the user during non-luteal menstrual phases of the menstrual cycle of the user.

20. The non-transitory computer readable medium of claim 17, wherein causing the insulin delivery device to administer insulin to the user comprises causing the insulin delivery device to administer the insulin to the user subsequent to the user approving the determined treatment.

* * * * *